United States Patent
Sutterer et al.

(10) Patent No.: US 10,543,186 B1
(45) Date of Patent: *Jan. 28, 2020

(54) CYSTEINE COMPOSITION AND INJECTION

(71) Applicant: Flamel Ireland Limited, Dublin (IE)

(72) Inventors: Angela Sutterer, Chesterfield, MO (US); Jill Simpson, Chesterfield, MO (US); Gauthier Pouliquen, Ternay (FR); Alain Constancis, Lyons (FR); Pierre Danner, Francheville (FR)

(73) Assignee: Flamel Ireland Limited, Dublin (IE)

( * ) Notice: Subject to any disclaimer, the term of this patent is extended or adjusted under 35 U.S.C. 154(b) by 0 days.

This patent is subject to a terminal disclaimer.

(21) Appl. No.: 16/373,255

(22) Filed: Apr. 2, 2019

Related U.S. Application Data (63) Continuation of application No. 16/355,028, filed on Mar. 15, 2019, now Pat. No. 10,493,051.

(51) Int. Cl.
| | | |
|---|---|---|
| *A61K 31/198* | (2006.01) | |
| *A61K 9/08* | (2006.01) | |
| *A61K 9/00* | (2006.01) | |
| *A61P 3/02* | (2006.01) | |

(52) U.S. Cl.
CPC .......... *A61K 31/198* (2013.01); *A61K 9/0019* (2013.01); *A61K 9/08* (2013.01); *A61P 3/02* (2018.01)

(58) Field of Classification Search
None
See application file for complete search history.

(56) References Cited

U.S. PATENT DOCUMENTS

| | | | |
|---|---|---|---|
| 6,051,567 | A | 4/2000 | Abrahamson et al. |
| 9,220,700 | B2 | 12/2015 | Savarese |
| 10,478,453 | B1 | 11/2019 | Maloney et al. |

OTHER PUBLICATIONS

Advenier; Aluminum contamination of parenteral nutrition and aluminum loading in children on long-term parenteral nutrition; J Ped Gastroenter Nutr; Apr. 2003; vol. 36(4); pp. 448-453.
Ahn; Mechanisms of Volatile Production from Sulfur-Containing Amino Acids by Irradiation; Rad Phys Chem; Oct. 2015; vol. 119; pp. 80-84.
Alcock; Norbornene probes for the study of cysteine oxidation; Tetrahedron; Nov. 2017; vol. 74; pp. 1220-1228.
Alemmari; Reduced aluminum contamination decreases parenteral nutrition associated liver injury; J Ped Surgery; Jan. 2012; vol. 47(5); pp. 889-894.
Allen; L-Cysteine Hydrochloride 50 mg/mL Injection; US Pharmacist; Sep. 2011; vol. 36(9); pp. 41-42.
Allwood; Compatibility and stability of additives in parenteral nutrition admixtures; Nutrition; 1998; vol. 14(9); pp. 697-706.
Apruzzese; Protonation Equilibria and Solubility of L-Cystine; Talanta; 2002; vol. 56; pp. 459-469.
Athilakshmi; Selective Detection of Cysteine/Cystine Using Silver Nanoparticles; Tet Lett; Nov. 2013; vol. 54; pp. 427-430.
Berthon; Trace metal requirements in TPN. 5. Formation constants for the Cu(II)-histidine ternary complexes with Thr, Lys, Gly, Phe, Val, Cys, and discussion of their implications regarding the Cu distribution in blood plasma during TPN and the evaluation of the daily dose of Cu; J Inorg Biochem; 1984; vol. 20, pp. 113-130.
Biavati; Complexing Agents and pH Influence on Chemical Durability of Type I Molded Glass Containers; PDA J Pharm Sci Technol; Jul.-Aug. 2017; vol. 71(4); pp. 306-316.
Biavati; Significance of Aluminum Release from Type I Borosilicate Glass Containers; Pharm Ind; 2010; vol. 72; pp. 2144-2147.
Bishop; Aluminum Neurotoxicity in Preterm Infancts Receiving Intravenous-Feeding Solutions; N Engl J Med; Mar. 1997; vol. 336(22); pp. 1557-1561.
Bjelton; Availability of cysteine and of L-2-oxo-thiazolidine-4-carboxylic acid as a source of cysteine in intravenous solution; JPEN J Parenter Enteral Nutr; Mar.-Apr. 1990; vol. 14; pp. 177-182.
Bohrer; Influence of the glass packing on the contamination of pharmaceutical products by aluminium. Part II: amino acids for parenteral nutrition; J Trace Elem Med Biol; 2001; vol. 15(2-3); pp. 103-108.
Bohrer; Contribution of the Raw Material to the Aluminum Contamination in Parenterals; JPEN J Parenter Enteral Nutr; 2002; vol. 26(6); pp. 382-388.
Bohrer; Influence of the Glass Packing on the Contamination of Pharmaceutical Products by Aluminum. Part III: Interaction Container—Chemicals During the Heating for Sterilization; J Trace Elem Med Biol; 2003; vol. 17(2); pp. 107-115.
Bohrer; Arsenic Release from Glass Containers by Action of Intravenous Nutrition Formulation Constituents; Int J Pharmaceutics; 2006; vol. 315; pp. 24-29.
Bohrer; Ion-exchange and potentiometric characterization of Al-cystine and Al-cysteine complexes; J Biol Inorg Chem; 2006; vol. 11; pp. 991-998.
Bohrer; Drugs as a hidden source of aluminium for chronic renal patients; Nephrol Dial Transport; 2007; vol. 22; pp. 605-611.
Bohrer; Low Availability of Aluminum in Formulations for Parenteral Nutrition Containing Silicate; JPEN J Parenter Enteral Nutr; Nov./Dec. 2009; vol. 33(6); pp. 694-701.
Bohrer; Aluminum loading in preterm neonates revisited; J Ped Gastroenter Nutr; Aug. 2010; vol. 51(2); pp. 237-241.
Boullata; A parenteral nutrition use survey with gap analysis; JPEN J Parenter Enteral Nutr; Mar. 2013; vol. 37(2); pp. 212-222.
Boullata; A.S.P.E.N. Clinical Guildelines: Parenteral Nutrition Ordering, Order Review, Compounding, Labeling and Dispensing; JPEN J Parenter Enteral Nutr; Mar. 2014; vol. 38(3); pp. 334-377.

(Continued)

*Primary Examiner* — Savitha M Rao
*Assistant Examiner* — Gregg Polansky
(74) *Attorney, Agent, or Firm* — Polsinelli PC (57) ABSTRACT

Cysteine compositions comprising less than about 400 μg/L of aluminum. For example, solutions of cysteine comprising a pharmaceutically acceptable solvent, cysteine, and less than about 145 μg/L of aluminum, wherein the solution is devoid of visible particulate matter. Cysteine compositions described herein may be suitable for injection. For example, disclosed cysteine solutions may be provided intravenously to meet amino acid nutritional requirement in individuals receiving total parenteral nutrition. Also provided are processes for preparing cysteine compositions, and methods for providing cysteine to individuals in need thereof.

28 Claims, 2 Drawing Sheets

(56) References Cited

OTHER PUBLICATIONS

Bukofzer; Industry perspective on the medical risk of visible particles in injectable drug products; PDA J Pharm Sci Technol; Jan.-Feb. 2015; vol. 69(1); pp. 123-139.
Cakir; Square-Wave Adsorptive Stripping Voltammetric Behavior of Fresh and Aged Cystine Solutions at Physiological pH; Electrochem Commun; 1999; vol. 1; pp. 257-261.
Cakir; Redox Behavior of Cysteine in the Presence of Ammonium Trixivanadate (V); Bioelectrochem; Mar. 2004; vol. 64; pp. 1-6.
Cakir; the Interaction of Cysteine with Chromium (VI) Ions Under UV Irradiation; Bioelectrochem; Apr. 2005; vol. 67; pp. 15-80.
Campanella; Simultaneous Determination of Cysteine, Cystine and 18 Other Amino Acids in Various Matrices by High-Perforamce Liquid Chromatography; J Chromatog A; 1999; vol. 833; pp. 137-145.
Cardiano; Thermodynamic and Spectroscopic Study of Al3+ Intercalation with Glycine, L-Cysteine and Tranexamic Acid in Aqueous Solution; Biophys Chem; Aug. 2017; vol. 230; pp. 10-19.
Carta; Solubilities of L-Cystine, L-Tyrosine, and Glycine in Aqueous Solutions at Varioius pHs and NaC1 Concentrations; J Chem Eng Data; 1996; vol. 41; pp. 414-417.
Chakraborty; Ground state vibrational spectra of cysteine and serine zwitterion: a theoretical prediction; J Molec Structure (Theochem); 1998; vol. 429; pp. 31-40.
Chen; Molecular Conformations of Crystalline L-Cysteine Determined with Vibrational Cross Angle Measurements; J Phys Chem; 2013; vol. 117; pp. 15614-15624.
Cochran; Prefilter and Postfilter Cysteine/Cystine and Copper Concentrations in Pediatric Parenteral Nutrition Solutions; JPEN J Parenter Enteral Nutr; Sep.-Oct. 1992; vol. 16(5); pp. 460-463.
Courtney-Martin; Plasma Aluminum Concentrations in Pediatric Patients Reciving Long-Term Parenteral Nutrition; JPEN J Parenter Enteral Nutr; Jul. 2015; vol. 39(5); pp. 578-585.
Csapo; Effect of pH on Stability and Plasmonic Properties of Cysteine-Functionalized Silver Nanoparticle Dispersion; Colloids Surf B: Biointerfaces; 2012; vol. 98; pp. 43-49.
Curry; Reducing the Risk of Contamination of Sterile Parenteral Products via Read-to-Use Closure Compenents; AAPS Pharm Sci Tech; Dec. 2010; vol. 11(4); pp. 1572-1579.
Dalton; The Solubilities of Certain Amino Acids in Water, the Densities of Their Solutions at Twenty-Five Degrees, and the Calculated Heats of Solution and Partial Molal Volumes; J Biol Chem; 1933; pp. 549-578.
De Cloet; Physicochemical stable standard all-in-one parenteral nutrition admixtures for infants and children in accordance with the ESPGHAN/ESPEN guidelines; Nutrition; 2018; vol. 49; pp. 41-47.
Dewey; Interconversion of Cystine and Cysteine induced by X-rays; Nature; 1965; vol. 206(4991); pp. 1369-1370.
Driscoll; Calculating Aluminum Content in Total Parenteral Nutrition Admixtures; Am J Health-Syst Pharm; Feb. 2005; vol. 62; pp. 312-315.
Drolshagen; Bis-tyrosyl-cystine—a potential source of tyrosine and cystine in parenteral nutrition; Clinical Nutrition; 1998; vol. 17; supplement 1; pp. 35.
Fewtrell; Symposium 2: Micronutrients Under the Microscope Aluminum Exposure from Parenteral Nutrients in Preterm Infancts and Later Health Outcomes During Childhood and Adolescence [Conference on 'Malnutrition matters']; Proc Nutr Soc; Jun. 2, 2011; vol. 70 pp. 299-304.
Flores-Huerta; Nature of Hydrogen Bonds and S—S Interactions in the L-Cystine Crystal; The Journal of Physical chemistry; Jun. 2016; vol. 120; pp. 4223-4230.
Freitas; Should pediatric parenteral nutrition be individualized?; Rev Paul Pediatr, 2014; vol. 32(4); pp. 326-332.
Fu; Inhibition of Growth of L-Cystine Crystals by N-Acetyl-L-Cysteine ; Cryst Eng Comm; 2016; vol. 18; pp. 8587-8590.
Gerwe; Studies on the Spontaenous Oxidation of Cysteine; J Biol Chem; 1931; vol. 91; pp. 57-62.
Guenter; Parenteral nutrition utilization: response to drug shortages; JPEN J Parenter Enteral Nutr; Jan. 2014; vol. 38 (1); pp. 11-12.
Gura; Aluminum contamination in products used in parenteral nutrition: has anything changed?; Nutrition; 2010; vol. 26 (6); pp. 585-594.
Gura; Aluminum contamination in parenteral products; Curr Opin Clin Nutr Metab Care; Nov. 2014; vol. 17(6); pp. 551-557.
Nascimento; Chromatography and Atomic Absorption Spectrometry for the Assessment of Heavy Metal Distribution among Amino Acids Used in Parenteral Nutrition Formulations—Studies with Cadmium and Lead; Biol Trace Elem Res; 2011; vol. 141; pp. 76-85.
Needham; The Solubility of Amino Acids in Various Solvent Systems; University of Rhode Island (Thesis); 1970; vol. 159; 95 pp.
Nehra; A.S.P.E.N. Clinical Guildelines: Nutrition Support of Neonatal Patients at Risk for Metabolic Bone Disease; JPEN J Parenter Enteral Nutr; 2013; vol. 37(5); pp. 570-598.
Obata; Studies on the Degradation Mechanisms of Proteins and Their Derivatives in the Foods ; Bull Agric Chem Soc Japan; 1960; vol. 24; pp. 562-564.
Ogawa; Comparisons of Aluminum and Silica Elution from Various Glass Vials; Chem Pharm Bull; 2016; vol. 64(2); pp. 150-160.
Oliveira; Aluminum Content in Intravenous Solutions for Administration to Neonates: Role of Product Preparation and Administration Methods; JPEN J Parenter Enteral Nutr; 2010; vol. 34; pp. 322-328.
O'Neal; Compliance with safe practices for preparing parenteral nutrition formulations; Am J Health-Syst Pharm; 2002; vol. 59; pp. 264-269.
Papanyan; Interaction of the L-Cysteine with Dimethyl Sulfoxide in Mild Conditions; Proc Yerevan State Univ Chem Biol; 2013; vol. 2; pp. 11-14.
Parikh; Physical Compatibility of Neonatal Total Parenteral Nutrient Admixtures Containing Organic Calcium and Inorganic Phosphate Salts; Am J Health-Syst Pharm; 2005; vol. 62; pp. 1177-1183.
Parker; Assignment of the vibrational spectrum of L-cysteine; Chem Phys; 2013; vol. 242; pp. 75-79.
Patel; Stability Considerations for Biopharmaceuticals, Part I; Bioprocess International; Jan. 2011; pp. 20-31.
Patrick; The Degradtive Metabolism of L-Cysteine and L-Cystine in Vitro by Liver in Cystinosis; Biochem J; 1962; vol. 83; pp. 248-256.
Pecul; Conformational Structures and Optical Rotation of Serine and Cysteine; Chem Physics Ltr; 2006; vol. 418; pp. 1-10.
Pereira-da-Silva; Calcium and phosphorus intake by parenteral nutrition in preterm infants; Diet Nutr Clitical Care; 2014; pp. 1-14.
Perez-Ruiz; Flow-Injection Successive Determination of Cysteine and Cystine in Pharmecutical Preparations; Talanta; 1991; vol. 38(11); pp. 1235-1239.
Pertkiewicz; Basics in clinical nutrition: Systems for parenteral nutrition, different systems for parenteral nutrition (AIO vs MB); e-SPEN Eur e-J Clin Nutr & Metab; 2009; vol. 4(3); pp. e123-e124.
Pillai; Pharmaceutical Glass Interactions: A Review of Possibilities; J Pharm Sci & Res; 2016; vol. 8(2); pp. 103-111.
Plogsted; Parenteral Nutrition L-Cysteine Product Shortage Considerations; Nutr Clin Practice; 2015; vol. 30(4); pp. 579-590.
Poole; Aluminum exposure from pediatric parenteral nutrition: meeting the new FDA regulation; JPEN J Parenter Enteral Nutr; May/Jun. 2008; vol. 32(3); pp. 242-246.
Poole; Aluminum in pediatric parenteral nutrition products: measured versus labeled content; J Pediatr Pharmacol Ther; 2011; vol. 16(2); pp. 92-97.
Poole; Aluminum Exposure in Neonatal Patients using the Least Contaminated Pn Solution products; Nutrients; 2012; vol. 4; pp. 1566-1574.
Ragab; Neonatal parenteral nutrition: Review of the pharmacist role as a prescriber; Saudi Pharm J; 2016; vol. 24; pp. 429-440.
Ralph; The Electrochemistry of L-Cystine and L-Cysteine; J Electronanal Chem; 1994; vol. 375; pp. 1-15.
Rassin; Essential and non-essential amino acids in neonatal nutrition; Prot Metab During Infancy (book); 1994; vol. 33 (Nestle Nutr Wkshp Series); pp. 183-195.

(56) References Cited

OTHER PUBLICATIONS

Read; The Kinetics and Mechanism of the Oxidation of S-Methyl-L-Cysteine, L-Cystine and L-Cysteine by Potassium Ferrate; Inorg Chim Acta; 2000; vol. 303; pp. 244-255.
Redher; Cysteine sulfenic acid as an intermediate in disulfide bond formation an non-enzymatic protein folding; Biochem; Sep. 2010; vol. 49(35); pp. 7748-7755.
Routh; The Decomposition of Cysteine in Aqueous Solution; J Biol Chem; 1939; vol. 130; pp. 297-304.
Salamon; Anaerobic Oxidation of Cysteine to Cystine by Magnese(III) in Aqueous Acetic Acid; Inorg Chim Acta; 2004; vol. 357; pp. 41-50.
Salles; Surface Damage in Cystine, an Amino Acid Dumer, Induced by keV Ions; J Chem Physics; 2018; vol. 148; pp. 1-8.
Schaut; Historical review of glasses used for parenteral packaging; PDA J Pharm Sci Technol; Jul.-Aug. 2017; vol. 71 (4); pp. 279-296.
Shelton; Plasma amino acid concentrations in 108 children receiving a pediatric amino acid formulation as part of parenteral nutrition; J Pediatr Pharmacol Ther; 2010; vol. 15(2); pp. 110-118.
Shinohara; The Stability of Cystine in Acid Solution; J Biol Chem; 1934; vol. 105; pp. 241-251.
Shkirskiy; The Effects of L-Cysteine on the Inhibition and Accelerated Dissolution Process of Zinc Metal; Corros Sci; 2015; vol. 100; pp. 101-112.
Smith; Effect of Additive Selection on Calculated Aluminum Content of Parenteral Nutrient Solutions; Am J Health-Syst Pharm; 2007; vol. 64(7); pp. 730-739.
Stawny; Pharmaceutical Point of View on Parenteral Nutrition; Scientific World J (Hindawi Publ Grp); vol. 2013; 9 pp.
Storey; Evaluation of Parenteral Nutrition Errors in an Era of Drug Shortages; Nutr Clin Practice; 2016; vol. 31(2); pp. 211-217.
Tarakeshwar; Vibrational Frequencies of Cysteineand Serine Zwitterions—an ab initio Assignment; Spectrochim Acta; 1995; vol. 51A(5); pp. 925-928.
Trivedi; The Role of Thiols and Disulfides in Protein Chemical and Physical Stability; Curr Prot Pept Sci; 2009; vol. 10 (6); pp. 614-625.
Unger; Stability & assessment of amino acids in parenteral nutrition solutions; J Pharma Biomed Ana; 2018; vol. 147; pp. 125-139.
Uthaya; Practical preterm parenteral nutrition: Systematic literature review & recommendations for practice; Early Human Development; 2014; vol. 90(11); pp. 747-753.
Veiga; Accumulation, elimination, and effects of parenteral exposure to aluminum in newborn and adult rats; J Inorg Biochem; 2013; vol. 128; pp. 215-220.
Weiss; Thermal Decomposition of the Amino Acids Glycine, Cysteine, Aspartic Acid, Asparagine, Glutamic Acid, Glutamine, Arginine and Histidine; BMC Biophysics; 2018; vol. 11(2); pp. 1-15.
Westin; Improved nutrition for extremely preterm infants—A population based observational study; Clinical Nutrition ESPEN; 2018; vol. 23; pp. 245-251.
Wier; Aluminum toxicity in neonatal parenteral nutrition: what can we do?; Annals Pharmacother; 2012; vol. 46(1); pp. 137-140.
Wright; Increased Incidence of Parenteral Nutrition-Associated Cholestasis with Aminosyn PF Compared to Trophamine; J Perinatology; 2003; vol. 23; pp. 444-450.
Yailian; Production and stability study of a hospital parenteral nutrition solution for neonates; J Pharm Analysis; 2018; 8 pp.
Yamagata; Determination of a small quantity of cystine in the presence of a large amount of cysteine; Biosci Biotech Biochem; 1999; vol. 63(8); pp. 1503-1505.
Yang; Design, Synthesis and Evaluation of L-Cystine Diamides as L-Cystine Crystallization Inhibitors for Cystinuria; Biorg Med Chem Lett; 2018; 6 pp.
Yarandi; Amino Acid Composition in Parenteral Nutritition: What is the Evidence?; Curr Opin Clin Nutr Metab Care; Jan. 2011; vol. 14(1); pp. 75-82.
Hager; Adsorption/Desorption Behavior of Cysteine and Cystine in Neutral and Basic Media: Electrochemical Evidence for Differing Thiol and Disulfide Adsorption to a Au(111) Single Crystal Electrode; J Electroanal Chem; 2003; vol. 550-551, pp. 291-301.
Hall; Infant Parenteral Nutrition Remains a Significant Source for Aluminum Toxicity; JPEN J Parenter Enteral Nutr; Mar. 2016; 6 pp.
Harigaya; Determination of aluminum in large volume parenteral drug products used in total parenteral nutrition therapy by ICP-MS with a dynamic reaction cell; Chem Pharm Bull; Apr. 2008; vol. 56(4); pp. 475-479.
Heacock; The infrared spectra of secondary amines and their salts; Can J Chem; 1956; pp. 1782-1795.
Hernández-Sánchez; Aluminium in parenteral nutrition: a systematic review; Eur J Clin Nutr; 2013; vol. 67(3); pp. 230-238.
Heyrovsky; The Reactions of Cystine at Mercury Electrodes; J Electroanal Chem; 1994; vol. 369; pp. 53-70.
Hirst; The Photochemical Degradation of Cystine in Aqueous Solution in the Presence of Air; Biochim Biophys Acta; 1969; vol. 184; pp. 345-357.
Huston; Aluminum Content of Neonatal Parenteral Nutrition Solutions: Options for Reducing Aluminum Exposure; Nutri in Clin Prac; Mar. 2016; pp. 1-5.
Huston; Calcium Chloride in Neonatal Parenteral Nutirtion Solutions with and without Added Cystein: Compatibility Studies Using Laser and Micro-Flow Imaging Methodology; PLOS One (open access); Aug. 2015; pp. 1-12.
Iacocca; Factors Affecting the Chemical Durability of Glass Used in the Pharmaceutical Industry; AAPS PharmSciTech; Sep. 2010; vol. 11(3); pp. 1340-1349.
Inglis; The Stability of Cysteine and Cystine during Acid Hydrolysis of Proteins and Peptides; J Biol Chem; Jan. 1970; vol. 245(1); pp. 112-116.
Jeppsson; One week's stability of TPN mixtures in plastic bags; Clinical Nutrition; 1987; vol. 6; pp. 155-160.
Jocelyn; The Standard Redox Potential of Cysteine-Cystine from the Thiol-Disulphide Exchange Reaction with Glutathione and Lipoic Acid; European J Biochem; 1967; vol. 2; pp. 327-331.
Kargosha; Vapour phase Fourier tranform infrared spectrometric determination of L-cysteine and L-cystine; Talanta; 2008; vol. 74; pp. 753-759.
Kato; Effects of the pH and Concentration on the Stability of Standard Solutions of Proteinogenic Amino Acid Mixtures; Analytical Sciences; 2017; vol. 33; pp. 1241-1245.
Klein; Parenteral drug products containing aluminum as an ingredient or a contaminant: response to FDA notice of Intent (Special ASCN/ASPEN Statement); Am J Clin Nutr; 1991; vol. 53; pp. 399-402.
Klein; The aluminum content of parenteral solutions: current status; Nutr Rev; 1991; vol. 49(3); pp. 74-79.
Klein; Aluminum and TPN-related bone disease; Am J Clin Nutr; 1994; vol. 55(2); pp. 483-485.
Klein; Aluminum contamination of parenteral nutrition solutions and its impact on the pediatric patient; Nutr Clin Practice; Aug. 2003; vol. 18(4); pp. 302-307.
Klein; Aluminum: new recognition of an old problem; Curr Opin Pharmacol; 2005; vol. 5(6); pp. 637-640.
Klish; Aluminum Toxicity in Infants and Children; Pediatrics (Am Acad Pediatrics); 1996; vol. 97(3); pp. 413-416.
Kostecka; Formulation of a Stable Parenteral Product; Clonidine HCI Injection; PDA J Pharm Sci Technol; 1998; vol. 52 (6); pp. 320-325.
Lanine; Cysteine usage increases the need for acetate in neonates who receive TPN; Talanta; 1991; vol. 54; pp. 565-567.
Lavine; The Iodometric Determination of Cysteine; J Biol Chem; 1935; vol. 109; pp. 141-145.
Lemma; Reactive Sulfur Species: Kinetics and Mechanism of the Equilibrium between Cysteine Sulfenyl Thiocyanate and Cysteine Thiosulfinate Ester in Acidic Aqueous Solution; J Org Chem; 2008; vol. 73; pp. 3017-3023.
Leung; Trace Elements in Parenteral Micronutrition; Clinical Biochem; 1995; vol. 28(6); pp. 561-566.
Lima-Rogel; Aluminum Contamination in Parenteral Nutrition Admixtures for Low-Birth-Weight Preterm Infants in Mexico; J Parenteral Enteral Nutri; Sep. 2016; vol. 40(7); pp. 1014-1020.

(56) References Cited

OTHER PUBLICATIONS

Lin; Dual Electrochemical Detection of Cysteine and Cystine in Capillary Zone Electrophoresis; J Chromatog A; 1994; vol. 680; pp. 263-270.
Liu; Kinetic Study of the Reaction Between Cystine and Sulfide in Alkaline Solutions; Can J Chem; 1987; vol. 65; pp. 770-774.
Loring; The Solubility of the Stereoisomers of Cystine with a Note on the Identity of Stone and Hair Cystine; J Biol Chem; 1934; vol. 107; pp. 267-274.
Lou; Kinetics and Mechanism of the Reaction of Cysteine and Hydrogen Peroxide in Aqueous Solution; J Pharm Sci; 2005; vol. 94(2); pp. 304-316.
Manning; Chemical stability of total parenteral nutrition mixtures; Int J Pharmaceutics; 1992; vol. 8, pp. 1-20.
Mascarenhas; Parenteral Nutrition; Pediatric Gastrointestinal and Liver Disease (book) 4th edition; 2011; Chapter 88; pp. 964-977.
Maya; Multifaceted Effects of Aluminium in Neurodegenerative Diseases: A Review; Biomed Pharmacother; 2016; vol. 33; pp. 746-754.
Migaki; Calcium chloride and sodium phosphate in neonatal parenteral nutrition containing TrophAmine: precipitation studies and aluminum content; JPEN J Parenter Enteral Nutr; Jul. 2012; vol. 36(4); pp. 470-475.
Mihailescu; The Effect of pH on Amino Acids Binding to Gold Nanoparticles; J Optoelectron Adv Mater; Mar. 2007; vol. 9 (3), pp. 756-759.
Mimica; Reversibility of the L-Cysteine/L-Cystine Redox Process at Physiological pH on Graphite Electrodes Modified with Coenzyme B12 and Vitamin B12; Electrochim Acta; 2002; vol. 48; pp. 323-329.
Mirtallo; A Nutrition Support Service Web Application to Manage Patients Receiving Parenteral Nutrition; Nutr Clin Practice; Aug./Sep. 2009; vol. 24(4); pp. 447-458.
Mirtallo; Aluminum contamination of parenteral nutrition fluids (Invited Commentary); JPEN J Parenter Enteral Nutr; May 2010; vol. 34(3); pp. 346-347.
Mirtallo; The Drug Shortage Crisis (Invited Commentary); JPEN J Parenter Enteral Nutr; Jul. 2011; vol. 35(4); p. 433.
Mirtallo; Consensus of Parenteral Nutrition Safety Issues and Recommendations; JPEN J Parenter Enteral Nutr; Mar. 2012; vol. 36(2); p. 625.
Mirtallo; Introduction and Goals of the Aspen Parenteral Nutrition Safety Summit; JPEN J Parenter Enteral Nutr; Mar. 2012; vol. 36(2); pp. 7S-9S.
Mirtallo; Parenteral nutrition ordering processes; JPEN J Parenter Enteral Nutr; Mar. 2012; vol. 36(2); pp. 29S-31S.
Mirtallo; Parenteral Nutrition Product Shortages: The A.S.P.E.N. Strategy; Nutr Clin Practice / J Pediatr Surg; 2012; vol. 27(3); pp. 385-391.
Mirtallo; Perspectives on parenteral micronutrient shortages; Nutr Clin Practice; Feb. 2015; vol. 30(1); pp. 86-91.
Missel; Chelating effect of novel pyrimidines in a model of aluminum intoxication; J inorg Biochem; 2005; vol. 99; pp. 1853-1857.
Monterroso-Marco; pH Effect on Cysteine and Cystine Behavior at Hanging Mercury Drop Electrode; Talanta; 2003; vol. 61; pp. 733-741.
Moreno; Aluminum in the neonate related to parenteral nutrition; Acta Paediatr; 1994; vol. 83(1); pp. 25-29.
Morgan; Early amino acid administration in very preterm infants: too little, too late or too much, too soon?; Seminars Fetal Neonatal Med; 2013; vol. 18(3); pp. 160-165.
Yokel; A Filtration System That Greatly Reduces Aluminum in Calcium Gluconate Injection, USP Used to Prepare Parenteral Nutrition Solutions; J Pediatr Pharmacol Ther; 2014; vol. 19(3); pp. 189-195.
Zlotkin; Cysteine supplementation to cysteine-free intravenous feeding regimens in newborn infants; Am J Clin Nutr; May 1981; vol. 34(5); pp. 914-923.
Sandoz L-Cysteine Hydrochloride—l-cysteine hydrochloride injection, solution product insert; 5 pp, Aug. 2018.
Sigma-Aldrich L-Cysteine hydrochloride monohydrate product info; 1 pp, May 2006.
Rohrer; Silicate release from glass for pharmaceutical preparations; Int J Phara; 2008; vol. 355; pp. 174-183.
Barnett; Basics in clinical nutrition: Parenteral nutrition admixtures, how to prepare PN admixtures; e-SPEN Eur e-J Clin Nutr & Metab; 2009; vol. 4; pp. e114-e116.
Exela; ELCYS (cysteine hydrochloride injection) product insert, Apr. 2019.
Sandoz; L-Cysteine hydrochloride injection product label, Jun. 2010.
Merck Index; 2779. Cysteine, 2780. Cystine, 1976, Ninth Edition, p. 364, Merck & Co., Ind., Rahway, N.J.
Taczkowska; ESI FT-MS and DFT Studies of Aqueous Au(I) Complexes with Cysteine and its Disulfide Form Cystine; Int J Mass Spec; 2016; vol. 406; pp. 12-19.
Office action dated Jul. 25, 2019 from related U.S. Appl. No. 16/355,028, 13 pp.
Sigma-Aldrich, "L-Cysteine hydrochloride monohydrate", 2 pages, downloaded on Jul. 6, 2019 from "https://www.sigmaaldrich.com/catalog/product/mm/102839?lang=en&region=US".
Abdulrazik et al., "Formulation for Slow Release of Oral Radiation-Protection Drugs," Int. J. Nucl. Med. Biol., 1984, pp. 53-54, vol. 11, No. 1.
Acetadote (acetylcysteine) injection, for intravenous use: Prescribing Information [Package Insert], Cumberland Pharmaceuticals Inc., Nashville, Tn (2017), pp. 1-12.
Aminosyn® II with Electrolytes [prescribing information and label], HOSPIRA, Inc., Lake Forest, IL, Revised: Oct. 2004, pp. 1-12.
Anderson et al., "Physical Compatibility of Calcium Chloride and Sodium Glycerophosphate in Pediatric Parenteral Nutrition Solutions," Journal of Parenteral and Enteral Nutrition, 2016, pp. 1166-1169, vol. 40, No. 8.
"ASHP Guidelines on the Safe Use of Automated Compounding Devices for the Preparation of Parenteral Nutrition Admixtures," Automation and Information Technology—Guidelines, pp. 63-67 (2000).
Ayers et al., "A.S.P.E.N. Parenteral Nutrition Safety Consensus Recommendations," Scholarship and Professional Work—COPHS, Butler University, 2014, pp. 1-64.
Baines et al., "The Association Between Cysteine, Bone Turnover, and Low Bone Mass," Calcif Tissue Int, 2007, pp. 450-454, vol. 81.
Bengoa et al., "Amino acid-induced hypercalciuria in patients on total parenteral nutrition," The American Journal of Clinical Nutrition, 1983, pp. 264-269, vol. 38.
Bettner et al., "Effects of pH, Temperature, Concentration, and Time on Particle Counts in Lipid-Containing Total Parenteral Nutrition Admixtures," Journal of Parenteral and Enteral Nutrition, 1986, pp. 375-380, vol. 10, No. 4.
Bistrian, "Brief History of Parenteral and Enteral Nutrition in the Hospital in the USA," Nestle Nutr Inst Workshop Ser Clin Perform Program, 2009, pp. 127-136, vol. 12.
Borges-Santos et al., "Plasma glutathione of HIV+ patients responded positively and differently to dietary supplementation with cysteine or glutamine," Nutrition, 2012, pp. 753-756, vol. 28.
Brigham et al., "The Concentrations of Cysteine and Cystine in Human Blood Plasma," J Clin Invest., 1960, pp. 1633-1638, vol. 39, No. 11.
Brown et al., "Potential Aluminum Exposure from Parenteral Nutrition in Patients with Acute Kidney Injury," Annals the of Pharmacotherapy, 2008, pp. 1410-1415, vol. 42, No. 10.
Bulbul et al., "Letter to the Editor: Nutritional support in preterm infants," Pediatrics and Neonatology, 2017, p. 562, vol. 58, No. 6.
Bullock et al., "Emulsion Stability in Total Nutrient Admixtures Containing a Pediatric Amino Acid Formulation," Journal of Parenteral and Enteral Nutrition, 1992, pp. 64-68, vol. 16, No. 1.
Calkins et al., "Effect of High-Dose Cysteine Supplementation on Erythrocyte Glutathione: a Double-Blinded, Randomized Placebo Controlled Pilot Study in Critically Ill Neonates," JPEN Journal of Parenteral and Enteral Nutrition, 2016, pp. 226-234, vol. 40, No. 2.
Connelly et al., "Congenital Hypothyroidism Caused by Excess Prenatal Maternal Iodine Ingestion," The Journal of Pediatrics, 2012, pp. 760-762, vol. 161, No. 4.

(56) References Cited

OTHER PUBLICATIONS

Courtney-Martin et al., "The Addition of Cysteine to the Total Sulphur Amino Acid Requirement as Methionine Does Not Increase Erythrocytes Glutathione Synthesis in the Parenterally Fed Human Neonate," Pediatric Research, 2010, pp. 320-324, vol. 67, No. 3.
"Cysteine," TOXNET: Toxicology Data Network, National Library of Medicine HSDB Database (2016), Retrieved from the Internet Nov. 25, 2019, <URL: https://toxnet.nlm.nih.gov/cgi-bin/sis/search/a?dbs+hsdb:@term+@DOCNO +2109>, 17 pgs.
Cysteine Hydrochloride Injection (prescribing information], Hospira 2004, Revised: Jun. 2013, Retrieved from the Internet Nov. 25, 2019, <URL: https://dailymed.nlm.nih.gov/dailymed/archives/fdaDrugInfo.cfm?archlveld=113819>, 4 pgs.
Darkwa et al., "Antioxidant Chemistry: Oxidation of L-Cysteine and Its Metabolites by Chlorite and Chlorine Dioxide," J. Phys. Chem. A, 2004, pp. 5576-5587, vol. 108, No. 26.
Delange, "Iodine deficiency in Europe and its consequences: an update," European Journal of Nuclear Medicine, 2002, pp. S404-S416, vol. 29, Supplement 2.
Delange, "Optimal Iodine Nutrition during Pregnancy, Lactation and the Neonatal Period," Int J Endocrinol Metab, 2004, pp. 1-12, vol. 2.
Delange, "Iodine requirements during pregnancy, lactation and the neonatal period and indicators of optimal iodine nutrition," Public Health Nutrition, 2007, pp. 1571-1580, vol. 10, No. 12A.
"Determination That Cysteine Hydrochloride Injection, USP, 7.25%, Was Not Withdrawn From Sale for Reasons of Safety or Effectiveness," Federal Register, Jun. 4, 2010; pp. 31790-31791, vol. 75, No. 107.
Dilger et al., "Excess Dietary L-Cysteine, but Not L-Cystine, Is Lethal for Chicks but Not for Rats or Pigs," The Journal of Nutrition, 2007, pp. 331-338, vol. 137, No. 2.
Domingo et al., "Risks of aluminium exposure during pregnancy," Contributions to Science, 2000, pp. 479-487, vol. 1, No. 4.
Dumortier et al., "Development of a Thermogelling Ophthalmic Formulation of Cysteine," Drug Development and Industrial Pharmacy, 2006, pp. 63-72, vol. 32, No. 1.
"Effect of Acetium® Capsules in Restoration of the Structure and Function of Gastric Mucosa After H. pylori Eradication in Patients with Atrophic Gastritis. A randomized, controlled trial.," Study Protocol, BIOHIT HealthCare, pp. 1-44 (2016).
El-Shenawy et al., "Nephrotoxicity of sodium valproate and protective role of L-cysteine in rats at biochemical and histological levels," J Basic Clin Physiol Pharmacol, 2016, pp. 497-504, vol. 27, No. 5.
Flora et al., "Chelation in Metal Intoxication," International Journal of Environmental Research and Public Health, 2010, pp. 2745-2788, vol. 7, No. 7.
Fortenberry et al., "Evaluating Differences in Aluminum Exposure through Parenteral Nutrition in Neonatal Morbidities," Nutrients, 2017, E1249, 6 pgs., vol. 9, No. 11.
Frey et al., "Confirming the Causative Role of Acetaminophen in Indeterminate Acute Liver Failure Using Acetaminophen—Cysteine Adducts," J. Med. Toxicol., 2015, pp. 218-222, vol. 11, No. 2.
Furst et al., "Parenteral nutrition by a solution of crystalline amino acids," Acta Med Scand Suppl., 1967, pp. 283-293, vol. 472.
Fusch et al., "Neonatology/Paediatrics—Guidelines on Parenteral Nutrition, Chapter 13," GMS German Medical Science, 2009, pp. 1-23, vol. 7.
Ghirri et al., "Iodine Supplementation in the Newborn," Nutrients, 2014, pp. 382-390, vol. 6.
"Guideline on the Use of Parenteral Nutrition in Neonatal and Paediatric Units," National Clinical Practice Guideline, Royal College of Physicians of Ireland, 46 pages, Publication date: Nov. 2016; Revision date: Nov. 2018.
"Guidelines for the Use of Parenteral and Enteral Nutrition in Adult and Pediatric Patients," Supplement to JPEN: Journal of Parenteral and Enteral Nutrition, Jan.-Feb. 2002, 149 pgs., vol. 26, No. 1.

Gura et al., "Recent developments in aluminium contamination of products used in parenteral nutrition," Current Opinion in Clinical Nutrition and Metabolic Care, 2006, pp. 239-246, vol. 9.
Hardy et al., "P.83: Stability of aqueous cysteine solutions for TPN [Abstract]," Clinical Nutrition, 1993, p. 61, vol. 12 (Suppl 2).
Hardy et al., "Formulation, Stability, and Administration of Parenteral Nutrition With New Lipid Emulsions," Nutrition in Clinical Practice, 2009, pp. 616-625, vol. 24, No. 5.
Harman et al., "Free Radical Metabolites of L-Cysteine Oxidation," The Journal of Biological Chemistry, 1984, pp. 5606-5611, vol. 259, No. 9.
Heird et al., "Pediatric Parenteral Amino Acid Mixture in Low Birth Weight Infants," Pediatrics, 1988, pp. 41-50, vol. 81, No. 1.
Hellstrom et al., "Sal863. L-Cysteine Slow-Release Capsule Formulation in Prevention of Gastric Carcinogenesis Associated With Atrophic Gastritis," AGA Abstracts, 2014, p. S-315, vol. 146.
Helms et al., "Cysteine supplementation results in normalization of plasma taurine concentrations in children receiving home parenteral nutrition," The Journal of Pediatrics, 1999, pp. 358-361, vol. 134, No. 3.
Heyman et al., "Aluminum Does Not Accumulate in Teenagers and Adults on Prolonged Parenteral Nutrition Containing Free Amino Acids," Journal of Parenteral and Enteral Nutrition, 1986, pp. 86-87, vol. 10, No. 1.
Ho et al., "Trend of Nutritional Support in Preterm Infants," Pediatrics and Neonatology, 2016, pp. 365-370, vol. 57, No. 5.
Hu et al., "Efficacy and safety of acetylcysteine in "non-acetaminophen" acute liver failure: A meta-analysis of prospective clinical trials," Clin Res Hepatol Gastroenterol, 2015, pp. 594-599, vol. 39, No. 5.
Huston et al., "Calcium chloride in neonatal parenteral nutrition: A 15 year experience," Journal of Neonatal-Perinatal Medicine, 2017, pp. 33-38, vol. 10, No. 1.
Huston et al., "Calcium Chloride in Neonatal Parenteral Nutrition: Compatibility Studies Using Laser Methodology," PLoS One, 2014, e106825, pp. 1-6, vol. 9, No. 9.
Ishii et al., "A case of drug-induced ductopenia resulting in fatal biliary cirrhosis," Liver, 1993, pp. 227-231, vol. 13.
Ishii et al., "Cystathionine γ-Lyase-deficient Mice Require Dietary Cysteine to Protect against Acute Lethal Myopathy and Oxidative Injury," The Journal of Biological Chemistry, 2010, pp. 26358-26368, vol. 285, No. 34.
Jadhav et al., "Parenteral Amino Acid and Metabolic Acidosis in Premature Infants," JPEN J Parenter Enteral Nutr., 2007, pp. 278-283, vol. 31, No. 4.
Janaky et al., "Mechanisms of L-Cysteine Neurotoxicity," Neurochemical Research, 2000, pp. 1397-1405, vol. 25, Nos. 9/10.
Ji et al., "Excessive L-cysteine induces vacuole-like cell death by activating endoplasmic reticulum stress and mitogen activated protein kinase signaling in intestinal porcine epithelial cells," Amino Acids, 2016, pp. 149-156, vol. 48, No. 1.
John et al., "Total parenteral nutrition usage trends in the United States," Journal of Critical Care, 2017, pp. 312-313, vol. 40.
Kartal et al., "Formulation and in-vivo evaluation of L-cysteine chewing gums for binding carcinogenic acetaldehyde in the saliva during smoking," Journal of Pharmacy and Pharmacology, 2007, pp. 1353-1358, vol. 59, No. 10.
Kartal et al., "Compatibility of chewing gum excipients with the amino acid L-cysteine and stability of the active substance in directly compressed chewing gum formulation," Journal of Pharmacy and Pharmacology, 2008, pp. 1131-1138, vol. 60, No. 9.
Kartal-Hodzic, "Formulation studies for eliminating saliva carcinogenic acetaldehyde with L-cysteine containing chewing gum," (Academic Dissertation), Division of Biopharmaceutics and Pharmacokinetics, University of Helsinki, Finland, 60 pages (2012).
Lee et al., "Introduction to the Revised American Association for the Study of Liver Diseases Position Paper on Acute Liver Failure 2011," Hepatology, 2012, pp. 965-967, vol. 55, No. 3.
Leung et al., "Consequences of excess iodine," Nature Reviews/Endocrinology, 2014, pp. 136-142, vol. 10, No. 3.
Leyden et al., "Stabilization of Solutions of Cysteine and its Derivatives," Canadian Journal of Biochemistry, 1967, pp. 611-614, vol. 45.

(56) References Cited

OTHER PUBLICATIONS

Li et al., "Acute and sub-chronic toxicity of glucose-cysteine Maillard reaction products in Sprague-Dawley rats," Food and Chemical Toxicology, 2015, pp. 271-276, vol. 80.

Look et al., "Is the Increase in Serum Cystathionine Levels in Patients with Liver Cirrhosis a Consequence of Impaired Homocysteine Transsulfuration at the Level of y-Cystathionase?," Scandinavian Journal of Gastroenterology, 2000, pp. 866-872, vol. 35, No. 8.

MacKay et al., "The Solubility of Calcium and Phosphate in Two Specialty Amino Acid Solutions," Journal of Parenteral and Enteral Nutrition, 1996, pp. 63-66, vol. 20, No. 1.

MacKay et al., "Physical Compatibility of Sodium Glycerophosphate and Calcium Gluconate in Pediatric Parenteral Nutrition Solutions," Journal of Parenteral and Enteral Nutrition, 2015, pp. 725-728, vol. 39, No. 6.

Malloy et al., "F48 Cysteine Supplementation During Total Parenteral Nutrition (TPN) [Abstract]," Clinical Nutrition, 1982, p. 49, vol. 1(Suppl.).

Malloy et al., "Cyst(e)ine measurements during total parenteral nutrition," The American Journal of Clinical Nutrition, 1983, pp. 188-191, vol. 37.

Malloy et al., "Total Parenteral Nutrition in Sick Preterm Infants: Effects of Cysteine Supplementation with Nitrogen Intakes of 240 and 400 mg/kg/day," Journal of Pediatric Gastroenterology and Nutrition, 1984, pp. 239-244, vol. 3, No. 2.

Malloy et al., "Cysteine Supplementation of Total Parenteral Nutrition: the Effect in Beagle Pups," Pediatric Research, 1984, pp. 747-751, vol. 18, No. 8.

Manz, "L-Cysteine in metabolic acidosis of low-birth-weight infants," American Journal of Clinical Nutrition, 1993, pp. 455-456, vol. 57, No. 3.

McCarthy et al., "Standardised versus Individualised Parenteral Nutrition. Further Food for Thought," Irish Medical Journal, 2016; 5 pgs. Retrieved Nov. 25, 2019 from: <https://www.lenus.ie/bitstream/handle/10147/620619/Standardised.html?sequence=1&isAllowed=y>.

McClave et al., "Guidelines for the Provision and Assessment of Nutrition Support Therapy in the Adult Critically Ill Patient: Society of Critical Care Medicine (SCCM) and American Society for Parenteral and Enteral Nutrition (A.S.P.E.N.)," Journal of Parenteral and Enteral Nutrition, 2016, pp. 159-211, vol. 40, No. 2.

Miller et al., "Decreased Cysteine and Proline Synthesis in Parenterally Fed, Premature Infants," Journal of Pediatric Surgery, 1995, pp. 953-958, vol. 30, No. 7.

Miller et al., "Parenteral Nutrition," U.S. Pharmacist, Published Jul. 20, 2006, 31 pages, HS10-HS20, vol. 7. [Retrieved from the Internet Nov. 25, 2019: <URL: https://www.uspharmacist.com/article/parenteral-nutrition].

Mirtallo et al., "Special Report: Safe Practices for Parenteral Nutrition," Journal of Parenteral and Enteral Nutrition, 2004, pp. S39-S70, vol. 28, No. 6.

Moreno Villares et al., "Current use of parenteral nutrition in a pediatric hospital. Comparison to the practise 8 years ago," Nutr. Hosp., 2005, pp. 46-51, vol. 20, No. 1.

Mundi et al., "Prevalence of Home Parenteral and Enteral Nutrition in the United States," Nutrition in Clinical Practice, 2017, pp. 799-805, vol. 32, No. 6.

Murphy et al., "Annual Summary of Vital Statistics: 2013-2014," Pediatrics, 2017, e20163239, pp. 1-12, vol. 139, No. 6.

Nguyen et al., "Effect of Increasing Glutathione With Cysteine and Glycine Supplementation on Mitochondrial Fuel Oxidation, Insulin Sensitivity, and Body Composition in Older HIV-Infected Patients," J Clin Endocrinol Metab, 2014, pp. 169-177, vol. 99, No. 1.

Niermeyer et al., "Optimized Calcium/Phosphorus Solubility in a Parenteral Nutrition Solution Containing Dicarboxylic Amino Acids and Cysteine." Journal of the American College of Nutrition, 1986, pp. 459-466, vol. 5.

Nishiyama et al., "Transient Hypothyroidism or Persistent Hyperthyrotropinemia in Neonates Born to Mothers with Excessive Iodine Intake," Thyroid, 2004, pp. 1077-1083, vol. 14, No. 12.

Olney et al., "Brain Damage in Infant Mice following Oral Intake of Glutamate, Aspartate or Cysteine," Nature, 1970, pp. 609-611, vol. 227.

Patanwala et al., "Antiemetic Therapy for Nausea and Vomiting in the Emergency Department," The Journal of Emergency Medicine, 2010, pp. 330-336, vol. 39, No. 3.

Patel et al., "Total parenteral nutrition for premature infants: practice aspects," Journal of Nature and Science, 2017, e301, pp. 1-6, vol. 3, No. 1.

Patt et al., "Cysteine Protection against X Irradiation," Science, 1949, pp. 213-214, vol. 110, No. 2852.

Paulikova et al., "Iodine toxicity in ruminants," Vet. Med.—Czech, 2002, pp. 343-350, vol. 47, No. 12.

Pertkiewicz et al., "Basics in clinical nutrition: Stability of parenteral nutrition admixtures," e-SPEN, the European e-Journal of Clinical Nutrition and Metabolism, 2009, pp. e117-e119, vol. 4.

PROSOL [prescribing information and label], Baxter Healthcare Corporation, Last revised: Sep. 3, 2015; pp. 1-21.

"The Provision of Parenteral Nutrition within Neonatal Services—A Framework for Practice," British Association of Perinatal Medicine, Apr. 2016, 27 pgs.

Pyati et al., "Absorption of iodine in the neonate following topical use of povidone iodine," The Journal of Pediatrics, 1977, pp. 825-828, vol. 91, No. 5.

Rabbini et al., "Glycation research in amino acids: a place to call home," Amino Acids, 2012, pp. 1087-1096, vol. 42.

Riedijk et al., "Cyst(e)ine Requirements in Enterally Fed Very Low Birth Weight Preterm Infants," Pediatrics, 2008, pp. e561-e567, vol. 121, No. 3.

Riedijk et al., "Cysteine: a conditionally essential amino acid in low-birth-weight preterm infants?," The American Journal of Clinical Nutrition, 2007, pp. 1120-1125, vol. 86.

Riedijk, "Neonatal Sulfur Amino Acid Metabolism," (Thesis), Erasmus Universiteit Rotterdam, the Netherlands, 176 pages, 2008.

Ripps et al., "Review: Taurine: A "very essential" amino acid," Molecular Vision, 2012, pp. 2673-2686, vol. 18.

Rubaltelli et al., "Parenteral Nutrition of the Newborn," Feeding the Sick Infant, Nestle Nutrition Workshop Series, 1987, pp. 241-255, vol. 11.

"Safe Practices for Parenteral Nutrition Formulations," National Advisory Group on Standards and Practice Guidelines for Parenteral Nutrition, Journal of Parenteral and Enteral Nutrition, 1998, pp. 49-66, vol. 22, No. 2.

Salaspuro et al., "Eliminating Carcinogenic Acetaldehyde by Cysteine From Saliva During Smoking," Cancer Epidemiology, Biomarkers & Prevention, 2006, pp. 146-149, vol. 15, No. 1.

Salaspuro et al., "Removal of Acetaldehyde from Saliva by a Slow-Release Buccal Tablet of L-Cysteine," International Journal of Cancer, 2002, pp. 361-364, vol. 97.

Sandilands et al., "Adverse reactions associated with acetylcysteine," Clinical Toxicology, 2009, pp. 81-88, vol. 47, No. 2.

Sawamoto et al., "L-Cysteine-induced brain damage in adult rats," Experimental and Toxicologic Pathology, 2004, pp. 45-52, vol. 56.

Sawamoto et al., "Four-Week Intravenous Repeated Dose Toxicity Study of L-Cysteine in Male Rats," The Journal of Toxicological Sciences, 2003, pp. 95-107, vol. 28, No. 2.

Sawamoto et al., "Development of Sperm Granulomas in the Epididymides of L-Cysteine-Treated Rats," Toxicologic Pathology, 2003, pp. 281-289, vol. 31, No. 3.

Schmidt et al., "Cost Containment Using Cysteine MC1 Acidification to Increase Calcium/Phosphate Solubility in Hyperalimentation Solutions," Journal of Parenteral and Enteral Nutrition, 1986, pp. 203-207, vol. 10, No. 2.

Schulpis et al., "L-Cysteine supplementation protects the erythrocyte glucose-6-phosphate dehydrogenase activity from reduction induced by forced training," Clinical Biochemistry, 2006, pp. 1002-1006, vol. 39.

Scientific Opinion on the safety and efficacy of L-cysteine hydrochloride monohydrate as a flavouring for pets, European Food Safety Authority (EFSA) Journal, 2013, 13 pages, vol. 11, No. 10.

Sears, "Chelation: Harnessing and Enhancing Heavy Metal Detoxification—A Review," The Scientific World Journal, 2013, 13 pages, vol. 2013.

(56) References Cited

OTHER PUBLICATIONS

Segal et al., "Delineation of Cystine and Cysteine Transport Systems in Rat Kidney Cortex by Developmental Patterns," PNAS, 1969, pp. 926-933, vol. 63.
Shew et al., "Improved Protein Metabolism in Neonates Receiving Parenteral Cysteine Supplementation," Pediatric Research, 1999, 2 pages, vol. 45(4).
Shew et al., "Assessment of cysteine synthesis in very low-birth weight neonates using a [13C6] glucose tracer," Journal of Pediatric Surgery, 2005, pp. 52-56, vol. 40.
Shulman et al., "Reply to F Manz," Am J Clin Nutr, 1993, p. 456, vol. 57, No. 3.
Shulman et al., "Parenteral Nutrition in Infants and Children," Journal of Pediatric Gastroenterology and Nutrition, 2003, pp. 587-607, vol. 36.
Sidhu et al., "L-Cysteine and Sodium Hydrosulphide Inhibit Spontaneous Contractility in Isolated Pregnant Rat Uterine Strips in vitro," Pharmacology & Toxicology, 2001, pp. 198-203, vol. 88.
Simmer et al., "Standardised Parenteral Nutrition," Nutrients, 2013, pp. 1058-1070, vol. 5.
Singer et al., "ESPEN Guidelines on Parenteral Nutrition: Intensive care," Clinical Nutrition, 2009, pp. 387-400, vol. 28.
Singh et al., "Physical compatibility of neonatal total parenteral nutrition admixtures containing organic calcium and inorganic phosphate salts in a simulated infusion at 37° C.", Pediatr Crit Care Med, 2009, pp. 213-216, vol. 10, No. 2.
Soghier et al., "Cysteine, cystine or N-acetylcysteine supplementation in parenterally fed neonates (Review)," Cochrane Database of Systematic Reviews, 2006, 39 pages, Issue 4, Art. No. CD004869.
Staun et al., "ESPEN Guidelines on Parenteral Nutrition: Home Parenteral Nutrition (HPN) in adult patients," Clinical Nutrition, 2009, pp. 467-479, vol. 28.
Stipanuk et al., "Mammalian Cysteine Metabolism: New Insights into Regulation of Cysteine Metabolism," Journal the of Nutrition, 2006, pp. 1652S-1659S, vol. 136 (6 Suppl).
Storm et al., "008 Cysteine Supplementation Normalizes Plasma Taurine Concentrations in Low Birth Weight Premature Infants Requiring Parenteral Nutrition Support [Abstract]," Nutrition Week 2003 Abstracts, pp. S4-S5, vol. 27, No. 1.
Sturman et al., "Absence of Cystathionase in Human Fetal Liver: Is Cystine Essential?," Science, 1970, pp. 74-76, vol. 169, No. 3940.
Szwergold et al., "Transglycation—A Potential New Mechanism for Deglycation of Schiffs Bases," Annals New York Academy of Sciences, 2005, pp. 845-864, vol. 1043.
Te Braake et al., "High-Dose Cysteine Administration Does Not Increase Synthesis of the Antioxidant Glutathione Preterm Infants," Pediatrics, 2009, pp. e978-e984, vol. 124, No. 5.
Telessy et al., "Kinetic stability of all-in-one parenteral nutrition admixtures in the presence of high dose Ca2+ additive under clinical application circumstances," Nutrition Journal, 2012, 5 pages, vol. 11, No. 32.
Thibault, "Possible Incompatibility between Amino Acids and Copper in Solutions for Pediatric Parenteral Nutrition," CJHP, 2014, pp. 160-164, vol. 67, No. 2.
Thomas, "Recommended Pinnacle® Compounder Ingredient Mixing Sequence," LDT Health Solutions, Inc., 2012, 4 pages.
Thomovsky et al., "Parenteral Nutrition: Formulation, Monitoring, and Complications," Compendium Contin Educ Vet., VetFolio, 2007, pp. 88-103, vol. 29, No. 2.
Thor et al., "Metabolic Activation and Hepatotoxicity—Effect of Cysteine, N-Acetylcysteine, and Methionine on Glutathione Biosynthesis and Bromobenzene Toxicity in Isolated Rat Hepatocytes," Archives of Biochemistry and Biophysics, 1979, pp. 405-413, vol. 192, No. 2.
Travasol [prescribing information and label], Baxter Healthcare Corporation, Rev: Nov. 2017, 20 pages.
Trissel et al., "Use of Cysteine Hydrochloride Injection to Increase the Solubility of Calcium and Phosphates in FreAmine III-Containing Parenteral Nutrition Solutions," International Journal of Pharmaceutical Compounding, 2003, pp. 71-77, vol. 7, No. 1.
"TrophAmine, [FDA prescribing information and label]," B. Braun Medical Inc., 20 pages, (2014). Retrieved Nov. 25, 2019 from <URL: https://www.drugs.com/pro/trophamine.html>.
Van Goudoever et al., "Amino Acid Solutions for Premature Neonates During the First Week of Life: The Role of N-Acetyl-L-Cysteine and N-Acetyl-L-Tyrosine," Journal of Parenteral and Enteral Nutrition, 1994, pp. 404-408, vol. 18, No. 5.
Vendemiale et al., "Effects of Oral S-Adenosyl-I-Methionine on Hepatic Glutathione in Patients with Liver Disease," Scandinavian Journal of Gastroenterology, 1989, pp. 407-415, vol. 24, No. 4.
Vina et al., "L-Cysteine and glutathione metabolism are impaired in premature infants due to cystathionase deficiency," Am J Clin Nutr, 1995, pp. 1067-1069, vol. 61, No. 5.
Vinton et al., "Taurine Concentrations in Plasma, Blood Cells, and Urine of Children Undergoing Long-Term Total Parenteral Nutrition," Pediatric Research, 1987, pp. 399-403, vol. 21, No. 4.
Warshawsky, "Intravenous Fat Emulsions in Clinical Practice," Nutrition in Clinical Practice, 1992, pp. 187-196, vol. 7, No. 4.
Watrobska-Swietlikowska et al., "Evaluation of physical stability of all in one parenteral admixtures for pediatric home care with high electrolytes concentrations," Nutr Hosp., 2015, pp. 236-243, vol. 31, No. 1.
Weinstein et al., "In Vivo Studies of Cysteine Metabolism," The Journal of Biological Chemistry, 1988, pp. 16568-16579, vol. 263, No. 32.
Whiting et al., "Effect of Headspace Oxygen Concentration on Growth and Toxin Production by Proteolytic Strains of Clostridium botulinum," Journal of Food Protection, 1992, pp. 23-27, vol. 55, No. 1.
Whyte et al., "Safety and Effectiveness of Acetadote for Acetaminophen Toxicity," The Journal of Emergency Medicine, 2010, pp. 607-611, vol. 39, No. 5.
Wilhelm et al., "Aluminum balance in intensive care patients," J. Trace Elements Med. Biol., 2001, pp. 223-227, vol. 14, No. 4.
Williams et al., "Supplemental Iodide for Preterm Infants and Developmental Outcomes at 2 Years: An RCT," Pediatrics, 2017, e20163703, 14 pages, vol. 139, No. 5.
Wlodek et al., "The Reaction of Sulfhydryl Groups with Carbonyl Compounds," Acta Biochimica Polonica, 1988, pp. 307-317, vol. 35, No. 4.
Woolsey, "Cysteine, Sulfite, and Glutamate Toxicity: A Cause of ALS?," The Journal of Alternative and Complementary Medicine, 2008, pp. 1159-1164, vol. 14, No. 9.
Yamaguchi et al., "Induction and Activation of Cysteine Oxidase of Rat Liver II. The Measurement of Cysteine Metabolism in vivo and the Activation of in vivo Activity of Cysteine Oxidase," Biochimica et Biophysica Acta, 1973, pp. 48-59, vol. 297, No. 1.
Yao et al., "Effect of glucose-cysteine adduct as a cysteine prodrug in rats," Amino Acids, 1997, pp. 85-94, vol. 12.
Yao et al., "Protective effect of glucose-cysteine adduct on the in situ perfused rat liver," Amino Acids, 1997, pp. 33-40, vol. 12.
Ybarra, "Calcium and Phosphate Solubility in Neonatal Parenteral Nutrient Solutions Containing TrophAmine," Nutrition in Clinical Practice, 2010, pp. 353-356, vol. 25, No. 4.
Yin et al., "L-Cysteine metabolism and its nutritional implications," Mol. Nutr. Food Res., 2015, pp. 1-13, vol. 0.
Zerangue et al., "Interaction of L-cysteine with a human excitatory amino acid transporter," Journal of Physiology, 1996, pp. 419-423, vol. 493, No. 2.
Zhang et al., "A Perspective on the Maillard Reaction and the Analysis of Protein Glycation by Mass Spectrometry: Probing the Pathogenesis of Chronic Disease," J Proteome Res., 2009, pp. 754-769, vol. 8, No. 2.
Zlotkin et al., "The Development of Cystathionase Activity During the First Year of Life," Pediatr. Res., 1982, pp. 65-68, vol. 16.

CYSTEINE COMPOSITION AND INJECTION

CROSS-REFERENCE TO RELATED APPLICATIONS

This application is a continuation of and claims priority to U.S. patent application Ser. No. 16/355,028, filed Mar. 15, 2019.

FIELD

The present disclosure relates to cysteine compositions having less than about 400 µg/L of aluminum and/or exhibiting extended stability.

BACKGROUND

Cysteine is considered a semi-essential amino acid for newborn infants and is routinely added to neonatal total parenteral nutrition (TPN) formulations. However, the stability of cysteine is low in solution, e.g., it can oxidize to form cystine, a disulfide dimer, which has a lower solubility than cysteine. Most crystalline amino acid solutions have pH levels of about 5-7, which would favor the conversion of cysteine to cystine. For these reasons, cysteine has typically been formulated as a separate parenteral nutrition additive and tends to be mixed with other TPN components just prior to use. Thus, preparations of cysteine with improved stability would be beneficial.

Aluminum is a contaminant commonly found in parenteral nutrition additive solutions. Research indicates that patients with impaired kidney function, including neonates, who receive parenteral levels of aluminum at greater than 4 to 5 µg per kg per day accumulate aluminum at levels associated with central nervous system and bone toxicity. In an attempt to limit the risk of aluminum toxicity, the U.S. Food and Drug Administration (FDA) has rules limiting the total aluminum content in TPN formulations. Since some preparations of cysteine can contain up to 5000 µg/L of aluminum, the total daily aluminum limit may be exceeded. Thus, preparations of cysteine with reduced levels of aluminum would also be beneficial.

SUMMARY

Among the various aspects of the present disclosure is the provision of solutions of cysteine, each of which includes a pharmaceutically acceptable solvent (e.g., water), cysteine (e.g., cysteine hydrochloride), and less than about 400 µg/L of aluminum. In some embodiments, the aluminum content may be substantially lower than 400 µg/L; for instance, the aluminum content of some embodiments may be less than about 145 µg/L, less than about 100 µg/L, less than about 30 µg/L, or even less than about 10 µg/L. In some embodiments, the aluminum content may range from about 0 µg/L to about 400 µg/L or from about 3 µg/L to about 145 µg/L. The aluminum content of some solutions described herein may be characterized with respect to specific storage conditions. For instance, the aluminum content of some embodiments may be less than about 400 µg/L when the solution is stored in a silica-lined vial i) for 6 months at 40° C. and 75% relative humidity or ii) for 18 months at 25° C. and 60% relative humidity.

Some of the above-described solutions exhibit relatively low pHs and/or include low levels of dissolved oxygen content. For instance, some solutions may have a pH from about 1.0 to about 2.5, a pH from about 1.0 to about 1.5, or a pH from about 1.0 to about 1.3. As another example, some solutions may have a dissolved oxygen content of less than 2 mg/L.

The solutions of cysteine set forth above may be devoid of visible particulate matter and/or precipitated particles of cystine. For instance, a solution may be devoid of visible particulate matter when stored for 18 months at 25° C. and 60% relative humidity. As another example, a solution may be devoid of visible particulate matter when stored for 6 months at 40° C. and 75% relative humidity.

Some embodiments of the solutions set forth above may be characterized as being sterile and/or formulated for injection (e.g., intravenous injection).

All of the features described above may exist individually or in any combination. For instance, in some embodiments, the solution may be characterized as having 50 mg/mL of cysteine hydrochloride monohydrate, less than 145 µg/L of aluminum, and a pH from about 1.0 to about 2.5, as well as being devoid of visible particulate matter.

Another aspect of the present disclosure provides a silica-lined vial having a solution of cysteine (such as any of those described above) disposed therein. The solution in the vial may be overlaid with a layer of nitrogen. The vial may be sealed in any appropriate manner (e.g., with a cap) and may include a pierceable septum or the like to enable the solution to be drawn therefrom for administration (e.g., intravenous administration) to individuals. In certain iterations, the solution in the vial comprises 50 mg of cysteine hydrochloride monohydrate per mL of water for injection adjusted to pH 1.0 to 2.5. In some iterations, the vial comprises 10 mL of the solution, which may or may not be required to be diluted prior to administration to an individual in need thereof.

Yet another aspect of the present disclosure encompasses a total parenteral nutrition formulation that includes a solution of cysteine described herein.

Still another aspect of the present disclosure provides a solution of cysteine having a cysteine monomer content of at least 99% by weight and a cystine dimer content of less than 1% by weight. The dissolved oxygen content of the solution may be less than about 2 mg/L, and the pH of the solution may be from about 1.0 to about 1.5. In some embodiments, the cystine dimer content of the solution may be less than about 0.5% by weight. The solution of this aspect is preferably devoid of precipitated particles of cystine dimer. In some embodiments of this aspect, the solution may have an aluminum content of less than about 400 µg/L or less than about 145 µg/L.

Still another aspect of the present disclosure provides processes for preparing cysteine having i) an aluminum content of less than about 400 µg/L (e.g., the aluminum content of any of the solutions of cysteine described above) and/or ii) a cystine dimer content of less than about 1% (or even less than about 0.05%) by weight. In this process, cysteine powder is added to a volume of a pharmaceutically acceptable solvent (e.g., water) to form a mixture. That mixture is mixed (e.g., stirred, agitated, or the like) to form a solution. The solution is then filtered to form a filtered solution, which can be dispensed into an appropriate container (e.g., a vial, such as a glass vial that may have an interior lining of silica). This process is preferably (but not necessarily) conducted under a nitrogen atmosphere.

In some embodiments of the above-described processes for preparing cysteine, the pharmaceutically acceptable solvent may be acidified (e.g., by addition of ⅛th molar equivalent of hydrochloric acid). This acidification typically (but not necessarily) would occur prior to adding the cysteine powder to the pharmaceutically acceptable solvent. As a result of this acidification, the pharmaceutically acceptable solvent preferably exhibits a pH well below 5. For instance, in some embodiments, the resulting pH of the pharmaceutically acceptable solvent may be between about 1.0 and about 2.5 (e.g., a pH of from about 1.0 to about 1.3).

Still with respect to the above-described processes for preparing cysteine, the pharmaceutically acceptable solvent may be degassed (e.g., by sparging same with nitrogen). In certain iterations, the dissolved oxygen content of the pharmaceutically acceptable solvent may be less than about 2 mg/L.

In some embodiments of the above-described processes for preparing cysteine, the filtered solution in the container may be overlaid with a layer of nitrogen, and the container may be sealed. In such embodiments, the filtered solution in the sealed container is preferably devoid of visible particulate matter. In some embodiments, the filtered solution in the sealed container may be characterized as being devoid of visible particulate matter i) after storage for 6 months at 40° C. and 75% relative humidity or ii) after storage for 18 months at 25° C. and 60% relative humidity.

Another aspect of the present disclosure encompasses a method for providing cysteine to a patient (e.g., neonate) in need of receiving total parenteral nutrition. In this method, the patient is administered a solution of cysteine described herein. The solution may be administered in any appropriate manner but is preferably administered intravenously. Further, the cysteine solution may be diluted (e.g., with saline, water for injection, and/or an amino acid solution) prior to administration to the patient.

Other aspects and features of the present disclosure are described in more detail below.

DETAILED DESCRIPTION

The present disclosure provides cysteine compositions having low levels of aluminum. In general, cysteine compositions disclosed herein are solutions comprising a pharmaceutically acceptable solvent, cysteine, and less than about 400 µg/L of aluminum. In some instances, cysteine solutions disclosed herein comprise less than about 145 µg/L of aluminum. Cysteine solutions described herein may be used as additives to amino acid solutions to meet nutritional requirements of individuals requiring total parenteral nutrition. Some cysteine solutions disclosed herein may be stable over time (i.e., the level of aluminum is essentially constant and the compositions remain free of visible particulate matter). Also provided herein are methods for preparing cysteine compositions, and methods of using cysteine compositions to provide cysteine to individuals in need thereof.

(I) Cysteine Compositions

One aspect of the present disclosure provides compositions comprising cysteine. The term "cysteine" as used herein refers to "L-cysteine." The "L" refers to the orientation of the chiral center of cysteine. All amino acids in the body are in the "L" configuration. Thus, L-cysteine and cysteine refer to the same moiety and the terms are often used interchangeably in clinical and nonclinical literature.

In general, the cysteine compositions disclosed herein are liquid compositions (e.g., solutions comprising cysteine dissolved in a pharmaceutically acceptable solvent). Suitable pharmaceutically acceptable solvents include water, acidified water, low concentration salt solutions, or saline solutions, which are of sufficient purity to be included in pharmaceutical formulations. The cysteine solution may further include hydrochloric acid and/or sodium hydroxide (e.g., to adjust the pH).

In general, the cysteine composition or solution has an aluminum content of less than about 400 µg/L. In certain embodiments, the aluminum content may be less than about 350 µg/L, less than about 300 µg/L, less than about 200 µg/L, or less than about 150 µg/L. In specific embodiments, the cysteine composition or solution may contain less than about 145 µg/L of aluminum. In various embodiments, the aluminum content may be less than about 140 µg/L, less than about 135 µg/L, less than about 130 µg/L, less than about 125 µg/L, less than about 120 µg/L, less than about 115 µg/L, less than about 110 µg/L, less than about 105 µg/L, less than about 100 µg/L, less than about 95 µg/L, less than about 90 µg/L, less than about 85 µg/L, less than about 80 µg/L, less than about 75 µg/L, less than about 70 µg/L, less than about 65 µg/L, less than about 60 µg/L, less than about 55 µg/L, less than about 50 µg/L, less than about 45 µg/L, less than about 40 µg/L, less than about 35 µg/L, less than about 30 µg/L, less than about 25 µg/L, less than about 20 µg/L, less than about 15 µg/L, less than about 10 µg/L, or less than about 5 µg/L. In still other embodiments, the aluminum content may range from about 0 µg/L to about 400 µg/L, from about 0 µg/L to about 145 µg/L, from about 0 µg/L to about 100 µg/L, from about 0 µg/L to about 30 µg/L, or from about 0 µg/L to about 10 µg/L.

In general, the cysteine composition or solution is essentially free of visible particulate matter. In specific embodiments, the cysteine composition or solution is devoid of visible particulate matter. "Visible particulate matter," as used herein, is defined as precipitated particles or crystals, irregularly shaped visible particles or crystals, or crystalline-like visible particles or crystals, but may also include fiber, dust, or other visible particle contaminants. In general, the visible particulate matter refers to particles or crystals of cystine, a disulfide dimer of cysteine (see Example 2), which forms in the presence of oxygen (air) and has reduced solubility at higher pH levels. The cysteine composition or solution may comprise a low percentage of cystine in solution but be devoid of particles of precipitated cystine. For example, in some embodiments, the cysteine composition or solution may comprise less than about 1% by weight of soluble cystine. In certain embodiments, the cysteine composition or solution may comprise less than about 0.9 wt %, less than about 0.8 wt %, less than about 0.7 wt %, less than about 0.6 wt %, less than about 0.5 wt %, less than about 0.4 wt %, less than about 0.3 wt %, less than about 0.2 wt %, or less than about 0.1 wt % of cystine in solution (and be devoid of particles of precipitated cystine).

The pH of the cysteine composition or solution may range from about 1.0 to about 2.5. In various embodiments, the pH of the cysteine composition or solution may range from about 1.0 to about 1.25, from about 1.25 to about 1.5, from about 1.5 to about 1.75, from about 1.75 to about 2.0, from about 2.0 to about 2.25, or from about 2.25 to about 2.5. In some embodiments, the pH of the cysteine composition or solution may be about 1.5 or less (e.g., may range from about 1.0 to about 1.5). In other embodiments, the pH of the cysteine composition or solution may be about 1.3 or less (e.g., may range from about 1.0 to about 1.3). In further embodiments, the pH of the cysteine composition or solution may be about 1.2 or less (e.g., may range from about 1.0 to about 1.2). In additional embodiments, the pH of the cysteine composition or solution may be about 1.1 or less (e.g., may range from about 1.0 to about 1.1). In specific embodiments, the pH of the cysteine composition or solution may be about 1.1, about 1.2, or about 1.3.

In general, the cysteine composition or solution may have a dissolved oxygen content of less than about 8 mg/L. In various embodiments, the dissolved oxygen content of the cysteine composition or solution may be less than about 7 mg/mL, less than about 6 mg/mL, less than about 5 mg/mL, less than about 4 mg/mL, less than about 3 mg/mL, less than about 2 mg/mL, less than about 1 mg/mL, less than about 0.8 mg/mL, less than about 0.6 mg/mL, less that about 0.4 mg/mL, or less than about 0.2 mg/mL. In specific embodiments, the dissolved oxygen content of the cysteine composition or solution may be less than about 2 mg/mL (or 2 ppm).

The cysteine composition or solution may contain a variety of forms of cysteine. For example, the cysteine composition or solution may contain cysteine free base or a pharmaceutically acceptable salt of cysteine. Pharmaceutically acceptable salts of cysteine include, without limitation, acetate, aspartate, benzoate, bitartrate, citrate, formate, gluconate, glucuronate, glutamate, fumarate, hydrochloride, hydrobromide, hydroiodide, hypophosphite, isobutyrate, isocitrate, lactate, malate, maleate, meconate, methylbromide, methanesulfonate, monohydrate, mucate, nitrate, oxalate, phenylpriopionate, phosphate, phthalate, propionate, pyruvate, salicylate, stearate, succinate, sulfate, tannate, tartrate, terephthalate, valerate, and the like. In exemplary embodiments, the cysteine composition or solution contains cysteine hydrochloride, the hydrochloride salt of cysteine. In specific embodiments, the cysteine composition or solution comprises cysteine hydrochloride monohydrate, which is the most soluble form of solid cysteine.

The concentration of cysteine in the cysteine composition or solution may vary. For example, the concentration of cysteine may range from about 10 mg/mL to about 100 mg/mL. In some embodiments, the concentration of cysteine in the cysteine composition or solution may be range from about 10-20 mg/mL, from about 20-40 mg/mL, from about 40-60 mg/mL, from about 60-80 mg/mL, or from about 80-100 mg/mL. In certain embodiments, the concentration of cysteine may range from about 40 mg/mL to about 60 mg/mL, from about 45 mg/mL to about 55 mg/mL, or from about 49 mg/mL to about 51 mg/mL. In specific embodiments, the cysteine composition or solution comprises cysteine hydrochloride and the concentration of cysteine hydrochloride in the composition or solution may be about 50 mg/mL.

In general, more than 99% by weight of the total amount of cysteine present in the composition or solution is monomeric (and less than 1% by weight of the total amount of cysteine in the composition or solution is a disulfide dimer, i.e., cystine). In various embodiments, more than 99.1 wt %, more than 99.2 wt %, more than 99.3 wt %, more than 99.4 wt %, more than 99.5 wt %, more than 99.6 wt %, more than 99.7 wt %, more than 99.8 wt %, or more than 99.9 wt % of the cysteine is monomeric.

The cysteine compositions or solutions disclosed herein may be dispensed into glass vials having a thin layer of silica on the interior surface (e.g., silica-lined vials), and wherein the composition or solution is overlaid with nitrogen prior to sealing of the glass vial. The glass vial may contain 4 mL, 6 mL, 10 mL, 15 mL, 20 mL, 30 mL, 40 mL, or 50 mL of the cysteine composition or solution. In specific embodiments, the vial contains 10 mL of cysteine composition or solution. For example, a vial may contain 10 mL of a 50 mg/mL solution of cysteine hydrochloride monohydrate in water adjusted to pH 1.0 to 2.5. In certain embodiments, more than one vial comprising the cysteine composition or solution is packaged together for distribution. For example, a package may comprise five 10-mL vials of cysteine composition or solution as disclosed herein.

The cysteine compositions or solutions, when dispensed into vials as described above, are substantially stable for at least one month, at least three months, at least six months, at least nine months, at least 12 months, at least 18 months, or at least 24 months when stored at 25° C. and 60% relative humidity or 40° C. and 75% relative humidity. Substantially stable means that the level of aluminum does not substantially change (e.g., does not increase) from the initial level present when the composition or solution was dispensed into the vial, and the composition or solution remains free of visible particulate matter. In particular embodiments, the composition or solution is substantially stable i) for at least 18 months when stored at 25° C. and 60% relative humidity or ii) for at least 6 months when stored at 40° C. and 75% relative humidity.

The cysteine compositions or solutions provided herein may be formulated in a variety of dosage forms. Suitable dosage forms include injectable formulations, or oral formulations. In some embodiments, the injectable formulation may be for parenteral administration, e.g., intravenous, intramuscular, intrathecal, and the like. In specific embodiments, the injectable formulation may be for intravenous administration.

In exemplary embodiments, the cysteine composition is a solution comprising 50 mg of cysteine hydrochloride monohydrate dissolved in one mL of water for injection that is adjusted to pH 1.0 to 2.5, and the solution of cysteine hydrochloride contains less than 145 µg/L of aluminum. US Pharmacopeia (USP) calls for not less than 85% and no more than 115% of the labeled amount of cysteine hydrochloride monohydrate. Thus, cysteine compositions labeled with a concentration of 50 mg/mL may contain from 42.5 mg/mL to 57.5 mg/mL of cysteine hydrochloride monohydrate.

The 50 mg/mL solution of cysteine hydrochloride monohydrate may have a dissolved oxygen content of less than 2 mg/L. The 50 mg/mL solution of cysteine hydrochloride monohydrate is devoid of visible particulate matter. In some embodiments, 10 mL of the 50 mg/mL cysteine hydrochloride monohydrate is packaged in a silica-lined glass vial. The 50 mg/mL solution of cysteine hydrochloride monohydrate is diluted prior to use (e.g., for use as an additive in total parenteral nutrition formulations). In general, the vial comprising the 50 mg/mL solution of cysteine hydrochloride monohydrate is stored at 20° C. to 25° C. (68° F. to 77° F.). In some embodiments, excursions to 15° C. to 30° C. (59° F. to 86° F.) are permitted [see USP Controlled Room Temperature]. In one embodiment, the vial is not frozen.

(II) Processes for Preparing Cysteine Compositions

Another aspect of the present disclosure encompasses processes for preparing the cysteine compositions disclosed herein. In general, the processes comprise (a) adding cysteine powder to water to form a mixture, (b) mixing the mixture until dissolution is complete, thereby forming a clear solution, (c) filtering the solution to form a filtered solution, and (d) dispensing the filtered solution into containers or vials, which are then sealed. To minimize oxygen exposure, all media (water, hydrochloric acid (HCl), sodium hydroxide) may be degassed by sparging with nitrogen, and the steps of the process may be conducted under nitrogen atmosphere (e.g., via use of a mixing bag or atmosbag under constant flow of nitrogen). All steps of the process generally are performed at ambient (e.g., room) temperature.

The water used in step (a) may be degassed to the desired level of dissolved oxygen by sparging with nitrogen. The degassed water may be acidified by adding HCl, wherein the HCl may have been degassed by sparging with nitrogen. The amount of HCl added to the water may vary. In some embodiments, the water may be acidified by adding $⅛^{th}$ molar equivalent of HCl. In other embodiments, the acidified water may be adjusted to have a concentration of 0.01 N HCl. In additional embodiments, the acidified water may have a pH of about 1.1. The level of dissolved oxygen and the pH of the acidified water may be monitored during this step of the process. The appropriate mass of cysteine powder is added a volume of acidified water that is close to the final volume needed to provide the desired concentration (thus, the concentration of cysteine at dissolution is nearly the same as the final desired concentration of cysteine).

The duration of mixing at step (b) may vary depending upon, for example, the concentration of cysteine, the volume of the mixture, and the like. The duration of mixing is generally just long enough to ensure complete dissolution of the cysteine, resulting in formation of a clear solution. Extended mixing times may lead to increased levels of dissolved oxygen in the resulting solution. The mixture may be mixed by stirring with a mixing blade or paddle. The rate of stirring can and will vary depending upon, for example, the concentration of cysteine, the volume of the mixture, and so forth. Upon complete dissolution, the pH of the clear solution may be monitored, and the pH may be adjusted by the addition of degassed HCl or degassed NaOH. The volume (or weight) of the clear solution may be adjusted such that the final concentration of cysteine is at the desired level. For example, additional degassed water may be added to the clear solution. As mentioned above, the mixing/dissolution step may be performed under nitrogen flow.

Step (c) comprises filtering the cysteine solution through at least one 0.22 μm filter. The filtration step may reduce the bioburden level in the cysteine solution and sterilize the solution. The filter may comprise polyvinylidene difluoride (PVDF), polyethersulfone (PES), cellulose nitrate, cellulose acetate or nylon. In specific embodiments, step (c) comprises serial filtration through two PVDF 0.22 μm filters. The filtration step may be performed under nitrogen flow.

The final step comprises dispensing the filtered cysteine solution into containers and sealing the containers. In general, the filtered cysteine solution is dispensed into silica-lined glass vials. The size or capacity of the vials may vary, and the volume of filtered cysteine solution dispensed into a vial may vary. In various embodiments, the volume of solution dispensed in a vial may be 4 mL, 6 mL, 10 mL, 15 mL, 20 mL, 30 mL, 40 mL, or 50 mL. In specific embodiments, vials are filled with 10 mL of the filtered cysteine solution. The filling may be performed under nitrogen flow.

Once filled with the appropriate volume, the cysteine solution generally is overlaid with nitrogen, and then the vial is sealed using conventional means. For example, the vial may be sealed with a cap, e.g., a cap comprising a pierceable septum. The filled vials generally are inspected to confirm the correct fill volume, check integrity of the sealing system, and confirm absence of particulates (e.g., visible cystine particles, fiber particles, dust particles). Vials not meeting these criteria are rejected.

The final vials that pass inspection may be packaged in multi-unit packages. For example, five 10 mL vials may be packaged into one package. Different numbers of vials and different sized vials can readily be packaged into multi-unit packages.

(III) Methods of Using Cysteine Compositions

Still another aspect of the present disclosure encompasses methods of using cysteine compositions disclosed herein to provide cysteine to individuals in need thereof. The disclosed cysteine compositions may be used to meet amino acid nutritional requirements in individuals receiving total parenteral nutrition. Provided herein are methods for providing cysteine to individuals in need thereof. In these methods, an injectable composition that includes cysteine is prepared by admixing a cysteine composition described herein with an amino acid injection composition. The injectable composition is then administered to the individual.

In general, the cysteine compositions disclosed herein can be used to meet amino acid nutritional requirements in individuals receiving total parenteral nutrition. In general, total parenteral nutrition tends to be administered intravenously (e.g., via central venous infusion). A cysteine composition described herein can be added to crystalline amino acid solution for administration as total parenteral nutrition following appropriate dilution. The crystalline amino acid solution generally includes the nine essential amino acids and may further comprise nonessential amino acids. Total parenteral nutrition can deliver a mixture of fluid, electrolytes, sugars, amino acids, vitamins, minerals, and often lipids to individual in need thereof.

Cysteine compositions disclosed herein may be provided to individuals who are unable to receive feedings or fluids by mouth or are unable to absorb nutrients through the gastrointestinal tract. In specific embodiments, the individual may be a neonate, which is an infant that is 28 days of less of age. In other embodiments, the individual may be a preterm infant, who is less than 28 days after term. In still other embodiments, the cysteine compositions may be administered to individuals with severe liver disease who may have impairment in the enzymatic conversion of cysteine. In such embodiments, the individual may be an infant, toddler or child less than 18 years of age.

The dose of cysteine can vary, depending (for example) on the total amount of amino acids administered to the individual. In general, the total amount of amino acids administered to a neonate via a total parenteral formulation may not exceed 3.5 grams of amino acids per kg per day. In general, the dose of cysteine may range from about 10 mg to about 50 mg of cysteine per gram of amino acid. In certain embodiments, the dose may be within the range of 15-20 mg of cysteine per gram of amino acid, the range of about 20-25 mg of cysteine per gram of amino acid, the range of about 25-30 mg of cysteine per gram of amino acid, or the range of about 30-40 mg of cysteine per gram of amino acid. In specific embodiments, the dose may be about 15 mg, about 22 mg, about 30 mg, or about 40 mg of cysteine per gram of amino acid.

In specific embodiments, cysteine compositions disclosed herein may be diluted with a solution of crystalline amino acids prior to administration to neonates receiving total parenteral nutrition. For example, an amino acid admixture may be prepared by adding the appropriate volume of a 50 mg/mL solution of cysteine hydrochloride monohydrate to a crystalline amino acid solution to provide cysteine at 2.2% of the total amino acids being supplied. Thus, a neonate receiving amino acids at 2.5 g/kg/day would be provided 55 mg/kg/day of cysteine or 1.1 mL/kg/day of 50 mg/mL cysteine solution; and a neonate receiving 3.0 g/kg/day of amino acids would be provided 1.3 mL/kg/day of 50 mg/mL cysteine solution.

Generally, the injectable composition may be prepared by aseptically diluting the amino acid admixture with appropriate caloric substrates (e.g., to supply the patient with adequate energy). The admixture may be inspected visually for particulate matter and discoloration prior to administration. The admixture may be refrigerated until ready for use and typically would be used within 24 hours of mixing. The injectable composition comprising cysteine may be administered intravenously. Those skilled in the art are familiar with means for administration as well as means for determining the rate of administration.

Definitions

When introducing elements of the embodiments described herein, the articles "a", "an", "the" and "said" are intended to mean that there are one or more of the elements. The terms "comprising", "including" and "having" are intended to be inclusive and mean that there may be additional elements other than the listed elements.

The term "about," generally is meant to encompass deviations of plus or minus five percent. However, when used in reference to a labeled pharmaceutical composition, it encompasses deviations of plus or minus fifteen percent (per USP guidelines). For example, a cysteine composition labeled with a concentration of 50 mg/mL may contain from 42.5 mg/mL to 57.5 mg/mL of cysteine hydrochloride monohydrate.

EXAMPLES

The following examples illustrate various embodiments of the present disclosure.

Example 1: Reduction in Aluminum Levels

Solutions of cysteine hydrochloride tend to be acidic (e.g., have a pH from ~1.0 to 2.5), suggesting that they could leach aluminum from standard borosilicate glass vials. To address this issue, several vial types were surveyed in a study (summarized in Table 1). In this study, aluminum content in 50 mg/mL solution of cysteine HCl was compared across various vials that were or were not subjected to terminal sterilization via heating. The study also evaluated aluminum content in the unapproved reference drug. The study showed that the use of Type I+ vials, which have an interior silica lining, greatly limited the aluminum content. In the study, aluminum contents in Type I+ vials were observed to be <10 µg/L for all samples and conditions tested, which is 2-3 orders of magnitude lower than observed for the reference drug product and for other unlined vial types.

TABLE 1

Summary of aluminum content results in different vial types subjected to different terminal sterilization conditions

| Sample | Vial size | Vial Type | Time Treated at 121° C. | Aluminum Content, µg/L |
|---|---|---|---|---|
| Bulk AV-FFP-17-0006 | NA | NA | None | 6.2 |
| AV-FFP-17-0006 | 10-mL | Type 1+, lined | None | 4.2 |
| | 10-mL | Type 1, unlined, molded | None | 33.9 |
| | 50-mL | Type 1, unlined, molded A | None | 17.4 |
| | 50-mL | Type 1, unlined, molded B | None | 26.3 |
| | 10-mL | Type 1+, lined | 20 min | 7.3 |
| | 10-mL | Type 1, unlined, molded | 20 min | 60.9 |
| | 50-mL | Type 1, unlined, molded A | 20 min | 52.5 |
| | 50-mL | Type 1, unlined, molded B | 20 min | 91.3 |
| Reference drug | 10-mL | Unknown | None | 427 |
| | 10-mL | Unknown | 20 min | 560 |

Example 2: Identification of Particulate Matter as Cystine

During scale-up production of cysteine hydrochloride, about 40-60% the API-filled vials were rejected during visual inspection because solid particles appeared after the vials were stored for several days at room temperature. The colorless, flat, irregularly shaped, crystalline-appearing particles were identified as cystine by a combination of Fourier Transform Infrared Spectroscopy (FTIR) and stereomicroscopy techniques.

Example 3: Solubility of Cysteine and Cystine

Cystine, a sulfur-sulfur dimer of cysteine, can form in the presence of oxygen (air) in cysteine solutions. Cystine, especially the free base, is several orders of magnitude less soluble in aqueous solutions than cysteine, and the solubility of cystine decreases as the pH increases. Thus, if enough cystine dimer is formed in the cysteine hydrochloride Injection drug product, the cystine may precipitate, or form undesirable particulates, in the solution. A summary of the solubility of the cystine and cysteine species is shown in Table 2.

TABLE 2

Summary of solubility results for cysteine and cystine species

| Species | Media | Solubility (mg/mL) at 22° C. |
|---|---|---|
| Cystine free base | Water | 0.14 |
| | Cysteine HCl Injection, 50 mg/mL | 0.59 |
| Cystine dihydrochloride | Water | 1.04 |
| | Cysteine HCl Injection, 50 mg/mL | 9.93 |
| Cysteine free base | Water | 18.74 |
| Cysteine hydrochloride | Water | 493.99 |

Furthermore, the solubility of cystine increases as the pH decreases. For example, at pH 1.4, the solubility of cystine is approximately 1 mg/ml, whereas at pH 1.0, its solubility increases to approximately 4 mg/mL (Carta et al., J Chem Eng Data, 1996, 41(3):414-417).

Example 4: Solubilization at 50 mg/mL at pH 1.1 or pH 1.3

To determine whether the formation of cystine particulates could be reduced, the process for preparing cysteine hydrochloride injection was modified by degassing solutions to reduce the levels of oxygen and adjusting the pH to a lower level. In particular, water was degassed by nitrogen sparging to reach various levels of dissolved oxygen (DO): 0.2 mg/L, 2.6 mg/ml, and 7.0 mg/mL. The pH of the final solution was 1.3-1.4. One part of the solution was adjusted to pH 1.1 by addition of 5N HCl (which had been degassed by nitrogen sparging). The water (at the different pH levels) was added to cysteine hydrochloride monohydrate powder at 50 mg/mL (under $N_2$ flow). The solution was stirred until dissolution was complete and the solution was clear. The solution was filtered, dispensed into (type 1+ silica lined) vials, and sealed under nitrogen. In order to have a reference at a saturated oxygen value, one vial of each series was exposed to air for several seconds before sealing. The protocol is outlined below in Table 3.

TABLE 3

Solubilization at 50 mg/mL

| pH adjustment | % DO/DO mg/L | Opened in the lab before sealing |
|---|---|---|
| No pH adjustment (~1.3) | 2.6%/0.22 mg/L | No |
| | | No |
| | | Yes |
| | | Kept open in the lab |
| | 29.4%/2.55 mg/L | No |
| | | No |
| | | Yes |
| | Aerated water 81.0%/7.02 mg/L | No |
| pH adjustment to ~1.1 | 2.6%/0.22 mg/L | No |
| | | No |
| | | Yes |
| | 29.4%/2.55 mg/L | No |
| | | No |
| | | Yes |

No particles were visible after 40 days in the vials sealed under nitrogen whatever the level of dissolved oxygen (DO) and whatever the pH. Particle formation was only observed for the vial left open in the lab. In increase in the level of dissolved oxygen is expected when vials are exposed to air.

Example 5: Solubilization at 58 mg/mL at pH 1.1, pH 1.3, or pH 1.5

Generally, cysteine HCl is prepared at an intermediate concentration (~58 mg/mL) and then adjusted to 50 mg/mL prior to filtration and bottling. Cysteine hydrochloride monohydrate powder was added under nitrogen flow to water degassed by nitrogen sparging (to reach 0.2 mg/L or 2.4 mg/L of dissolved oxygen). The pH was about 1.3 in the final solution. In one fraction, the pH of the solution was adjusted to pH 1.1 by addition of 5N HCl (previously degassed by nitrogen sparging). In another fraction, the pH was adjusted to 1.5 with 0.1 N NOH (previously degassed). The solutions were stirred until dissolution was complete, diluted to 50 mg/ml with water (previously degassed), filtered, and filled into (lined) vials, which were then sealed under nitrogen. In order to have a reference at a saturated oxygen value, one vial of each series was exposed to air, and one vial of each series was kept open in the lab.

TABLE 4

Solubilization at 58 mg/mL

| pH adjustment | % DO/DO mg/L | Opened in the lab before sealing |
|---|---|---|
| No pH adjustment (~1.3) | 2.4%/0.22 mg/L | Yes |
| | | No |
| | | No |
| | | Kept open in the lab |
| | 27.3%/2.43 mg/L | Yes |
| | | No |
| | | No |
| pH adjusted to ~1.1 | 2.4%/0.22 mg/L | Kept open in the lab |
| | | Yes |
| | | No |
| | | No |
| | 27.3%/2.43 mg/L | Kept open in the lab |
| | | Yes |
| | | No |
| | | No |
| pH adjusted to ~1.3 | 2.4%/0.22 mg/L | Kept open in the lab |
| | | Yes |
| | | No |
| | | No |
| | 27.3%/2.43 mg/L | Kept open in the lab |
| | | Yes |
| | | No |
| | | No |
| | | Kept open in the lab |

Figure 1:
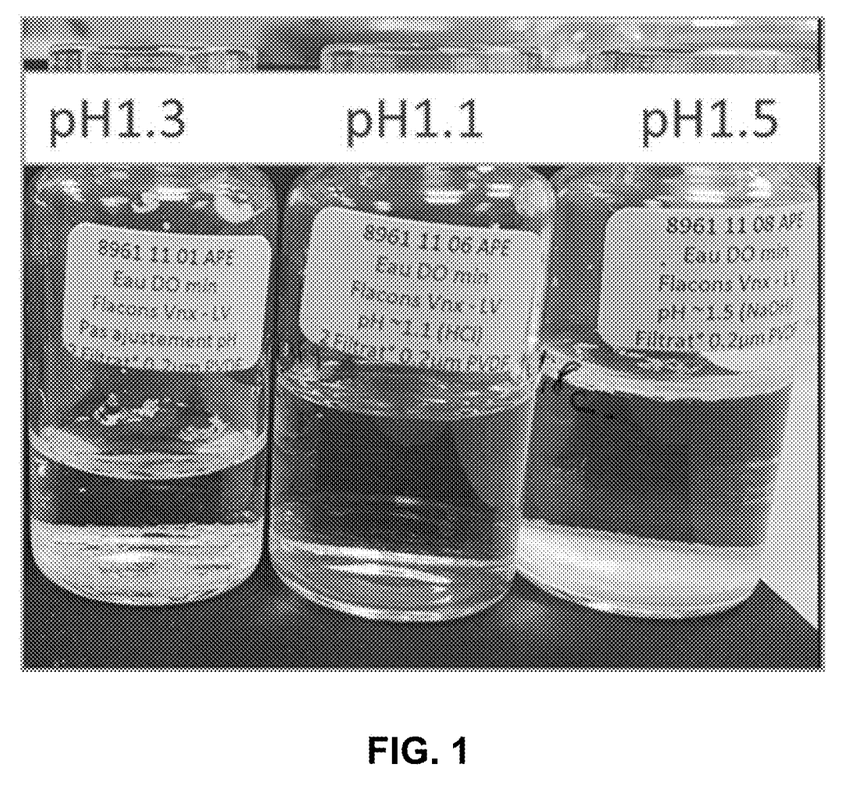
FIG. 1 presents an image of vials kept open to air for 25 days. Cysteine was dissolved at a concentration of 58 mg/mL. The pH of the solution was not adjusted (pH 1.3), was adjusted to pH 1.1 with hydrochloric acid, or was adjusted to pH 1.5 with sodium hydroxide.

No particles were visible (observation over 80 days) in the vials sealed under nitrogen whatever the level of dissolved oxygen (DO) and whatever the pH. In contrast, many particles appeared in samples exposed or kept open in air at pH 1.3 or 1.5 after 5 to 13 days (FIG. 1). A few particles were also observed after 25 days at pH 1.1. HCl (5M) was added to the pH 1.3 samples exposed to air (many particles) to decrease the pH to 1.1. A complete dissolution of the particles was observed after 8 hr without stirring, presumably due to re-solubilization of cystine at the lower pH.

The following conclusion can be drawn from the data of Examples 4 and 5: (i) air exposure and oxidation foster particle formation, (ii) acidic pH appears to slow down oxidation and cystine precipitation, and (iii) an intermediate concentration of 58 mg/mL appears to promote particle formation.

Example 6: Comparative Study

A study was undertaken to directly compare (i) 50 mg/mL vs. 58 mg/mL dissolution concentration of cysteine HCl, (ii) dissolution in water vs. dissolution in acidic water (addition of 5N HCl to obtain a final concentration of 0.01 N HCl), and (iii) 15 min vs. 90 min duration of stirring during dissolution. All experiments were carried out in parallel and launched the same day using Type 1+ silica-lined vials. All steps were performed under nitrogen with low dissolved oxygen levels (less than 0.5 mg/L). For each series, 3 vials were sealed under nitrogen and one vial was exposed to air to assess accelerated oxidizing conditions.

Figure 2A:
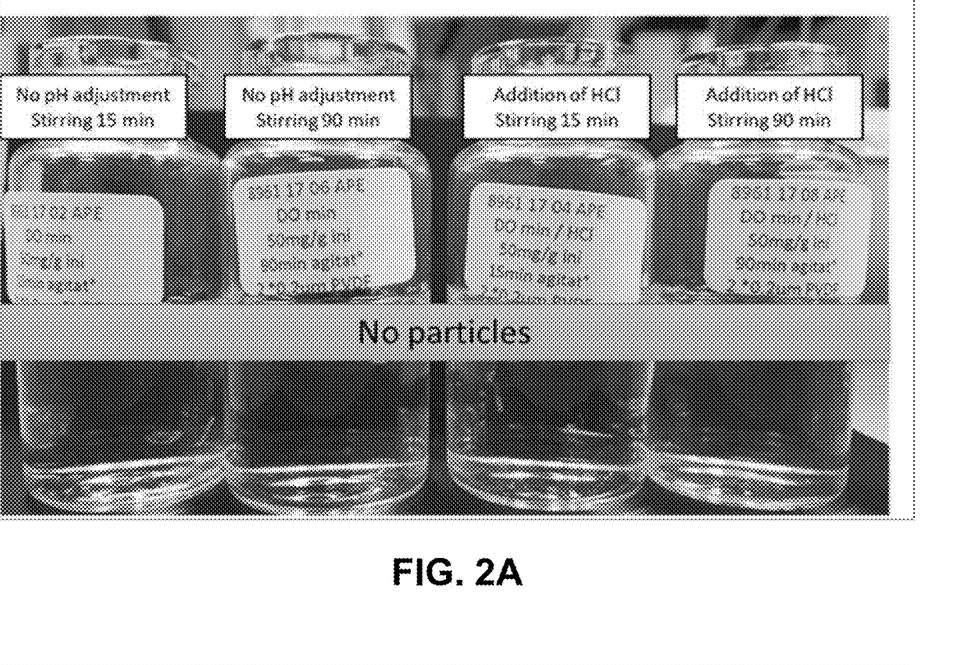
FIG. 2A shows an image of vials after being open in the lab for 14 days. Cysteine was dissolved in water (with no pH adjustment) or in acidified water (addition of HCl) at a concentration of 50 mg/ml with stirring for 15 or 90 minutes.
Figure 2B:
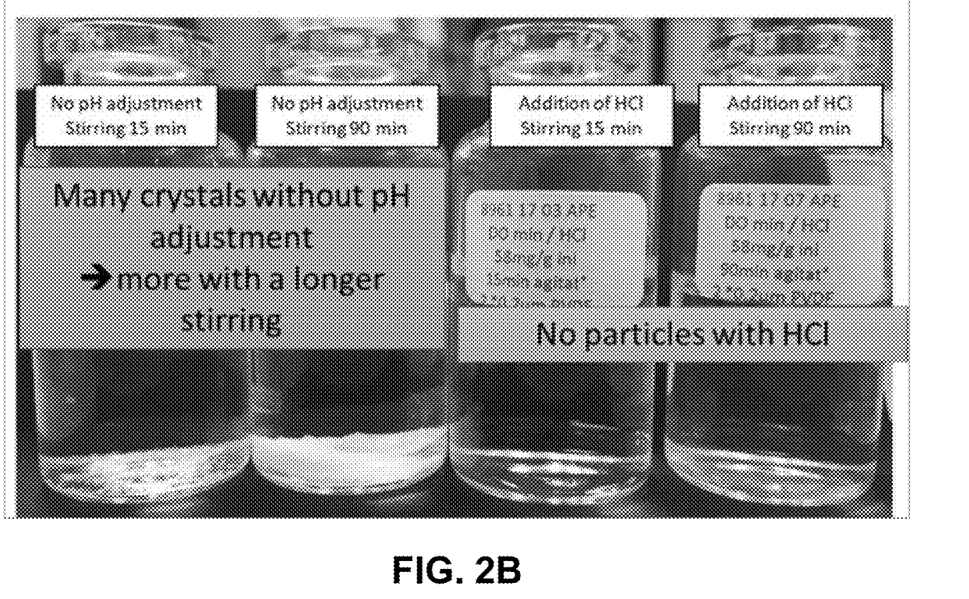
FIG. 2B shows an image of vials after being open in the lab for 14 days. Cysteine was dissolved in water (with no pH adjustment) or in acidified water (addition of HCl) at a concentration of 58 mg/ml with stirring for 15 or 90 minutes.

No particles were observed after 66 days under any condition for the vials sealed under nitrogen. In vials left open, particles were observed after 7 days in those with no pH adjust and high dissolution concentration (58 mg/mL). FIGS. 2A and 2B presents images at 14 days in vials kept open in the lab. For these samples, the duration of stirring increased the abundance of particles in vials with higher pH (i.e., those without pH adjustment) (FIG. 2B). On the contrary, decreasing the pH to about 1.1 helped prevent formation of particles whatever the stirring duration (FIG. 2A).

In samples without pH adjustment and exposed to air for longer than 14 days, particles were observed after 37 days in those dissolved at 50 mg/mL and stirred for 90 min. Particles were observed after 66 days in those dissolved at 50 mg/mL and stirred for 15 min. In contrast, no particles were observed after 66 days in samples with a more acidic pH (pH 1.1), regardless of dissolution concentration and stirring duration.

From the studies described above, the manufacturing process was modified to ensure that all steps were conducted in low oxygen environment, all liquids were degassed to reduce dissolved oxygen levels, and the initial water used to dissolve the cysteine was acidified. Adopting these changes reduced the percentage of rejected vials (e.g., containing particulates) per batch as high as about 50% to less than about 0.05%.

Example 7: Stability Studies

Vials of 50 mg/mL of cysteine HCl from various batches were stored at room temperature and assayed at selected time points. The data are presented below in Table 5. (1 ppb=1 µg/L)

TABLE 5

Stability at room temperature

| Sample | Time | Cysteine | Cystine | Aluminum |
|---|---|---|---|---|
| Lab Batch, lined vial | 18 mo | 100.8% | 1.2% | <3 ppb |
| Batch 1700141, unlined vial | 12 mo | 99.7% | 1.05% | 182 ppb |
|  | 18 mo | 97.5% | 1.23% | 370 ppb |
| Batch 1700196, unlined vial | 6 mo | 98.4% | 0.84% | 189 ppb |
|  | 12 mo | 98.2% | 1.17% | 273 ppb |
| Batch 1800029, lined vial | 6 mo | 98.5% | 0.83% | <3 ppb |
|  | 9 mo | 97.8% | 0.91% | <3 ppb |
| Batch 1800030, lined vial | 6 mo | 98.6% | 0.91% | <3 ppb |
|  | 9 mo | 96.7% | 0.98% | <3 ppb |
| Batch 1800031, lined vial | 6 mo | 98.2% | 1.00% | <3 ppb |
|  | 9 mo | 95.6% | 1.10% | <3 ppb |
| Lab batch, low pH, lined vial | 3 mo | 101.2% | 0.19% | <3 ppb |
| Batch 1800172, lined vial | 0 mo | 99.2% | 0.46% | <3 ppb |
| Batch 1800229, lined vial | 0 mo | 98.1% | 0.66% | <3 ppb |

What is claimed is:

1. A method of using a cysteine solution, wherein the cysteine solution i) comprises cysteine hydrochloride in water for injection, ii) has a pH from about 1.0 to about 2.5, iii) has an aluminum content of less than about 145 micrograms per liter, and iv) is devoid of visible particulate matter, and wherein the method comprises:
   (a) diluting the cysteine solution; and
   (b) intravenously administering the diluted cysteine solution to a patient in need thereof.

2. The method of claim 1, wherein the aluminum content of the cysteine solution is less than about 125 micrograms per liter.

3. The method of claim 1, wherein the diluting comprises diluting the cysteine solution with saline, water for injection, an amino acid solution, or a combination thereof.

4. The method of claim 1, wherein the diluting comprises mixing the cysteine solution with an amino acid solution.

5. The method of claim 4, wherein the diluted cysteine solution comprises about 10-50 milligrams of cysteine per gram of amino acid.

6. The method of claim 1, wherein diluted cysteine solution further comprises electrolytes.

7. The method of claim 1, wherein the patient has severe liver disease.

8. The method of claim 1, wherein the patient is i) unable to receive feeding or fluid by mouth or ii) is unable to absorb nutrients through the gastrointestinal tract.

9. The method of claim 1, wherein the patient is an infant.

10. The method of claim 4, wherein cysteine makes up 2.2% of the total amino acid content of said diluted cysteine solution.

11. The method of claim 1, wherein the intravenously administering occurs within 24 hours of the diluting.

12. The method of claim 1, further comprising refrigerating the diluted cysteine solution prior to the intravenously administering.

13. The method of claim 1, wherein the L-cysteine solution has been passed through at least one 0.22 µm filter.

14. A method of using a cysteine solution, wherein the cysteine solution i) comprises a pharmaceutically acceptable solvent, ii) has a cysteine hydrochloride concentration of about 50 milligrams per milliliter, iii) has a pH from about 1.0 to about 1.5, iv) has an aluminum content of less than about 200 micrograms per liter, and v) is devoid of visible particulate matter due, at least in part, to the pH being from about 1.0 to about 1.5, and wherein the method comprises:
   (a) diluting the cysteine solution with saline, water for injection, an amino acid solution, or a combination thereof; and
   (b) intravenously administering the diluted cysteine solution to a patient in need thereof, wherein the patient is i) a neonate or infant, ii) unable to receive feeding or fluid by mouth, iii) unable to absorb nutrients through the gastrointestinal tract, or iv) has severe liver disease.

15. The method of claim 14, wherein the aluminum content of the cysteine solution is less than about 145 micrograms per liter.

16. The method of claim 14, wherein the diluting comprises mixing the cysteine solution with an amino acid solution.

17. The method of claim 16, wherein the diluted cysteine solution comprises from about 10-50 milligrams of cysteine per gram of amino acid.

18. The method of claim 14, wherein diluted cysteine solution further comprises electrolytes.

19. A method of using a cysteine solution having a monomeric cysteine content of at least 99% by weight of total cysteine present in the solution and a dimeric cystine content of less than 1% by weight of total cysteine present in the solution, wherein the cysteine solution has a dissolved oxygen content of less than about 2 mg/L, a pH from about 1.0 to about 2.5, and is devoid of visible particulate matter, and wherein the method comprises:
   (a) diluting the cysteine solution with saline, water for injection, an amino acid solution, or a combination thereof; and
   (b) parenterally administering the diluted cysteine solution to a patient in need thereof, wherein the patient is i) a neonate or infant, ii) unable to receive feeding or fluid by mouth, iii) unable to absorb nutrients through the gastrointestinal tract, or iv) has severe liver disease.

20. The method of claim 19, where the cysteine solution contains less than about 145 micrograms of aluminum per liter.

21. The method of claim 19, wherein the cysteine solution comprises cysteine hydrochloride monohydrate in water for injection.

22. The method of claim 19, wherein the diluting comprises diluting the cysteine solution with an amino acid solution.

23. The method of claim 22, wherein the diluted cysteine solution comprises from about 10-50 milligrams of cysteine per gram of amino acid.

24. The method of claim 19, wherein the parenterally administering occurs within 24 hours of the diluting.

25. The method of claim 19, further comprising refrigerating the diluted cysteine solution prior to the parenterally administering.

26. The method of claim 19, wherein the cysteine solution has a pH from about 1.0 to about 1.5 prior to the diluting.

27. The method of claim 19, wherein the diluted cysteine solution parenterally administered further comprises electrolytes.

28. The method of claim 19, wherein the diluted cysteine solution parenterally administered further comprises sugars, vitamins, trace minerals, lipids, or a combination thereof.

\* \* \* \* \*